United States Patent
Bar-Sagi et al.

(10) Patent No.: US 11,209,420 B2
(45) Date of Patent: Dec. 28, 2021

(54) CANCER DIAGNOSTICS, THERAPEUTICS, AND DRUG DISCOVERY ASSOCIATED WITH MACROPINOCYTOSIS

(71) Applicant: New York University, New York, NY (US)

(72) Inventors: Dafna Bar-Sagi, Miller Place, NY (US); Cosimo Commisso, New York, NY (US); Rengin De Chey, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 15/990,030

(22) Filed: May 25, 2018

(65) Prior Publication Data
US 2018/0335420 A1    Nov. 22, 2018

Related U.S. Application Data

(62) Division of application No. 14/009,013, filed as application No. PCT/US2012/031828 on Apr. 2, 2012, now Pat. No. 9,983,194.

(60) Provisional application No. 61/470,945, filed on Apr. 1, 2011.

(51) Int. Cl.
| | |
|---|---|
| *G01N 33/50* | (2006.01) |
| *G01N 33/574* | (2006.01) |
| *A61K 31/352* | (2006.01) |
| *A61K 31/192* | (2006.01) |
| *A61N 5/10* | (2006.01) |
| *A61K 45/06* | (2006.01) |
| *A61K 31/685* | (2006.01) |
| *A61K 31/5377* | (2006.01) |
| *A61K 31/4965* | (2006.01) |
| *A61K 31/435* | (2006.01) |
| *A61K 31/4178* | (2006.01) |
| *A61K 31/407* | (2006.01) |
| *A61K 31/366* | (2006.01) |
| *A61K 38/00* | (2006.01) |

(52) U.S. Cl.
CPC ....... *G01N 33/5005* (2013.01); *A61K 31/192* (2013.01); *A61K 31/352* (2013.01); *A61K 31/366* (2013.01); *A61K 31/407* (2013.01); *A61K 31/4178* (2013.01); *A61K 31/435* (2013.01); *A61K 31/4965* (2013.01); *A61K 31/5377* (2013.01); *A61K 31/685* (2013.01); *A61K 45/06* (2013.01); *A61N 5/10* (2013.01); *G01N 33/5011* (2013.01); *G01N 33/574* (2013.01); *A61K 38/00* (2013.01); *G01N 2800/7028* (2013.01)

(58) Field of Classification Search
CPC ......... G01N 2800/7028; G01N 33/574; G01N 33/5011
See application file for complete search history.

(56) References Cited

U.S. PATENT DOCUMENTS

| | | |
|---|---|---|
| 6,214,824 B1 | 4/2001 | Evans et al. |
| 2004/0208880 A1 | 10/2004 | Kumar et al. |
| 2009/0215692 A1 | 8/2009 | Das Gupta et al. |
| 2011/0311584 A1 | 12/2011 | Sahin et al. |

FOREIGN PATENT DOCUMENTS

WO    2006036410 A2    4/2006

OTHER PUBLICATIONS

Overmeyer et al. Mol Cancer Res 2008;6(6). Jun. 2008, pp. 965-977 (Year: 2008).*
Xu et al. Effect of dimethyl amiloride on invasive activity of highly-metastatic lung carcinoma cell line and its possible mechanisms, Zhongliu (2009) 29 (12), 1107-1111, English abstract from STN search (Year: 2009).*
Britannica Online Differences between a Peptide and a Protein 2020, https://www.britannica.com/story/what-is-the-difference-between-a-peptide-and-aprotein#:~:text=Peptides%20are%20smaller%20than%20proteins,50%20or%20more%20amino%20acids. (Year: 2020).*
Gold et al., "A Clathrin Independent Macropinocytosis-Like Entry Mechanism Used by Bluetongue Virus-1 During Infection of BHK Cells," PLoS One, 5(6)(e11360):1-14 (2010).
Barr et al., "Clathrin Independent Endocytosis of ErbB2 in Geldanamycin-Treated Human Breast Cancer Cells," J. Cell Sci., 121(19):3155-3166 (2008).
Koumakpayi et al., "Macropinocytosis Inhibitors and Arf6 Regulate ErbB3 Nuclear Localization in Prostate Cancer Cells," Molecular Carcinogenesis, 50:901-912 (2011).
International Search Report and Written Opinion for PCT/US2012/031828, dated Nov. 16, 2012.
Moser et al., "A Kinome RNAi Screen Identified AMPK as Promoting Poxvirus Entry Through the Control of Actin Dynamics," PLoS Pathog. 6(6):e1000954 (2010).
Nishimura et al., "Combinatorial Targeting of the Macroponocytotic Pathway in Leukemia and Lymphoma Cells," J Biol. Chem. 283(17):11752-11762 (2008).
Overmeyer et al., "Active Ras Triggers Death in Glioblastoma Cells through Hyperstimulation of Macropinocytosis", Mol Cancer Res 6(6):965-977 (2008).
Johannes L. Bos, "Ras Oncogenes in Human Cancer: A Review", Cancer Research 49:4682-4689 (1989).
Brognard et al., "Akt/Protein Kinase B Is Constitutively Active in Non-Small cell Ling Cancer Cells and Promotes Cellular Survival and Resistance to Chemotherapy and Radiation", Cancer Research 61:3986-3997 (2001).
Bruewer et al., "Interferon-Gamma Induces Internalization of Epithelial Tight Junction Proteins via a Macropinocytosis-like Process", The FASEB Journal 19(8):923-933 (2005).

(Continued)

*Primary Examiner* — Kortney L. Klinkel
*Assistant Examiner* — William Y Lee
(74) *Attorney, Agent, or Firm* — Troutman Pepper Hamilton Sanders LLP (Rochester)

(57) ABSTRACT

The present invention is directed to methods of inhibiting both proliferation and survival of cancer cells and for treating a subject having cancer. The present invention is further directed to methods of diagnosing cancer in a subject and identifying cancer therapeutics.

7 Claims, 26 Drawing Sheets

Specification includes a Sequence Listing.

(56) References Cited

OTHER PUBLICATIONS

Cardone et al., "The Role of Disturbed pH Dynamics and the Na+/H+ Exchanger in Metastasis", Nature Rev. Cancer 5:786-795 (2005).
Grunicke et al., "Role of Na+/H+-Antiporter in Growth Stimulation by Ha-ras", Plasma Membrane Oxidoreductases in Control of Animal and Plant Growth NATO ASI Series 7:369-381 (1988).
V. Craig Jordan, "Tamoxifen: A Most Unlikely Pioneering Medicine" Nature Reviews: Drug Discovery 2:205-213 (2003).
Xu et al., Effect of Dimethyl Amiloride on Invasive Activity of Highly-Metastatic Lung Carcinoma Cell Line and its Possible Mechanisms, Zhongliu 29(12):1107-111 (2009) (English abstract from STN search).

\* cited by examiner

A

B $$\text{SURVIVAL RATIO} = \frac{\text{VIABILITY}^{TET[x]}}{\text{VIABILITY}^{TET[50]}}$$

SURVIVAL = VIABILITY$^{BSA[x\%]}$
RATIO        VIABILITY$^{BSA[0.4\%]}$

A. EIPA Treatment of H-RasV12-Expressing Cells in Low BSA 10, 1, and 0µl EIPA for each day B. EIPA Treatment of H-RasV12-Expressing Cells in 2% BSA 25, 10, and 0 µl EIPA for each day $$\text{SURVIVAL RATIO} = \frac{\text{VIABILITY}^{\text{NO DOX}}}{\text{VIABILITY}^{\text{DOX}}}$$

FIG. 16 A-B
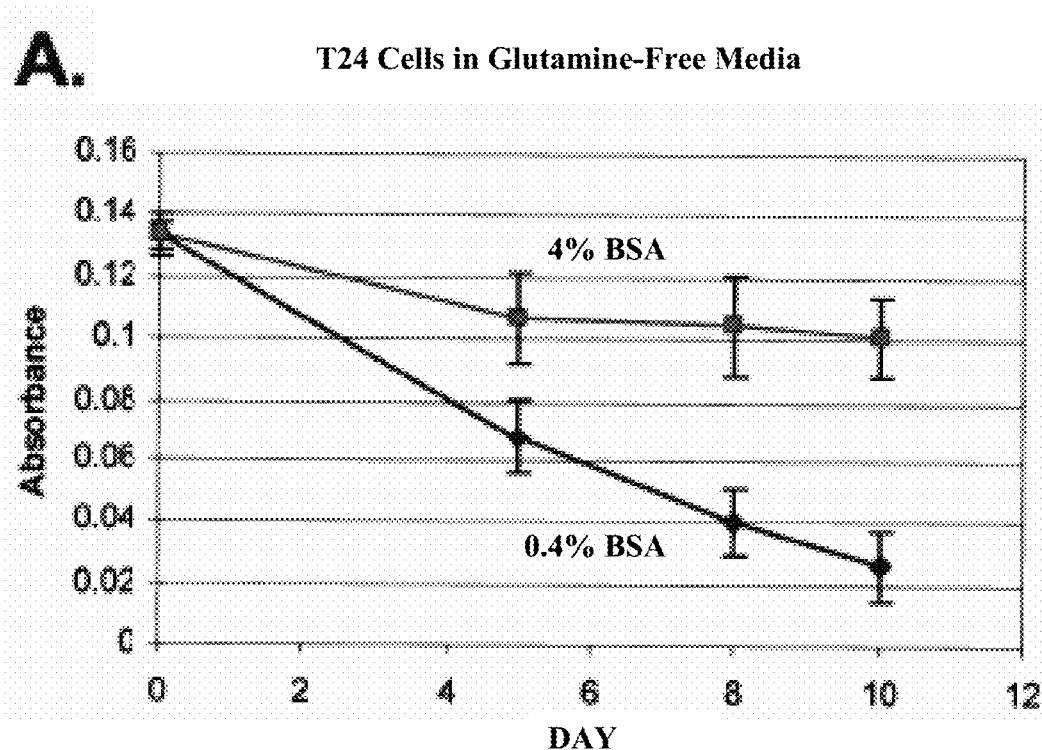
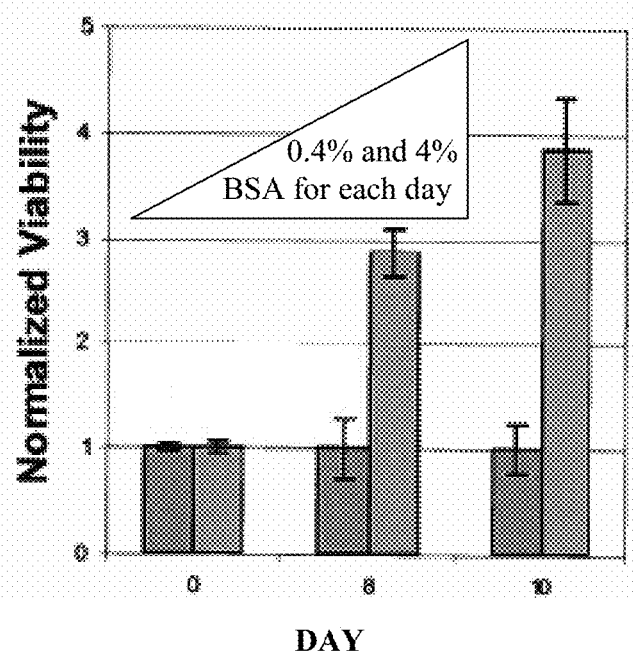

FIG. 16 C-D
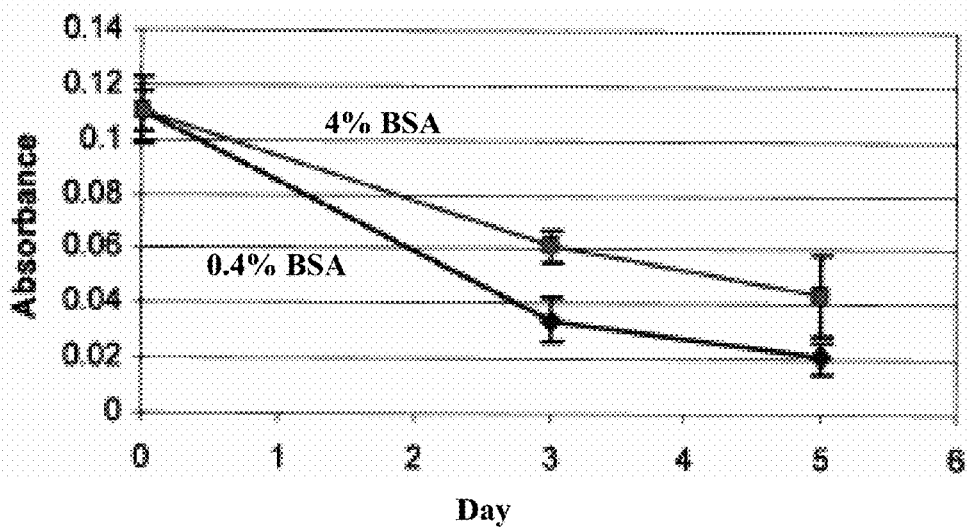
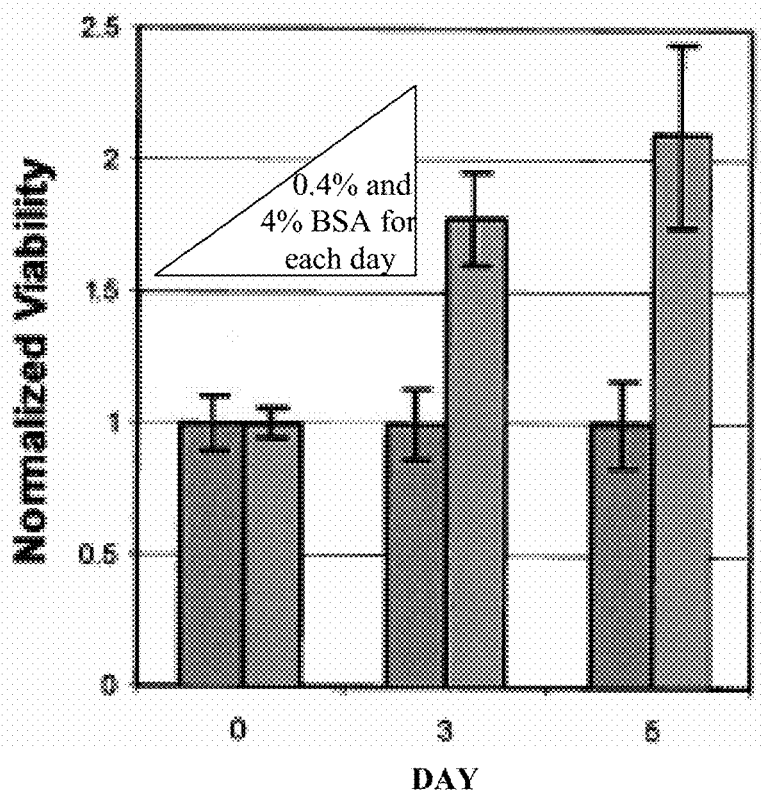

FIG. 20 B-C
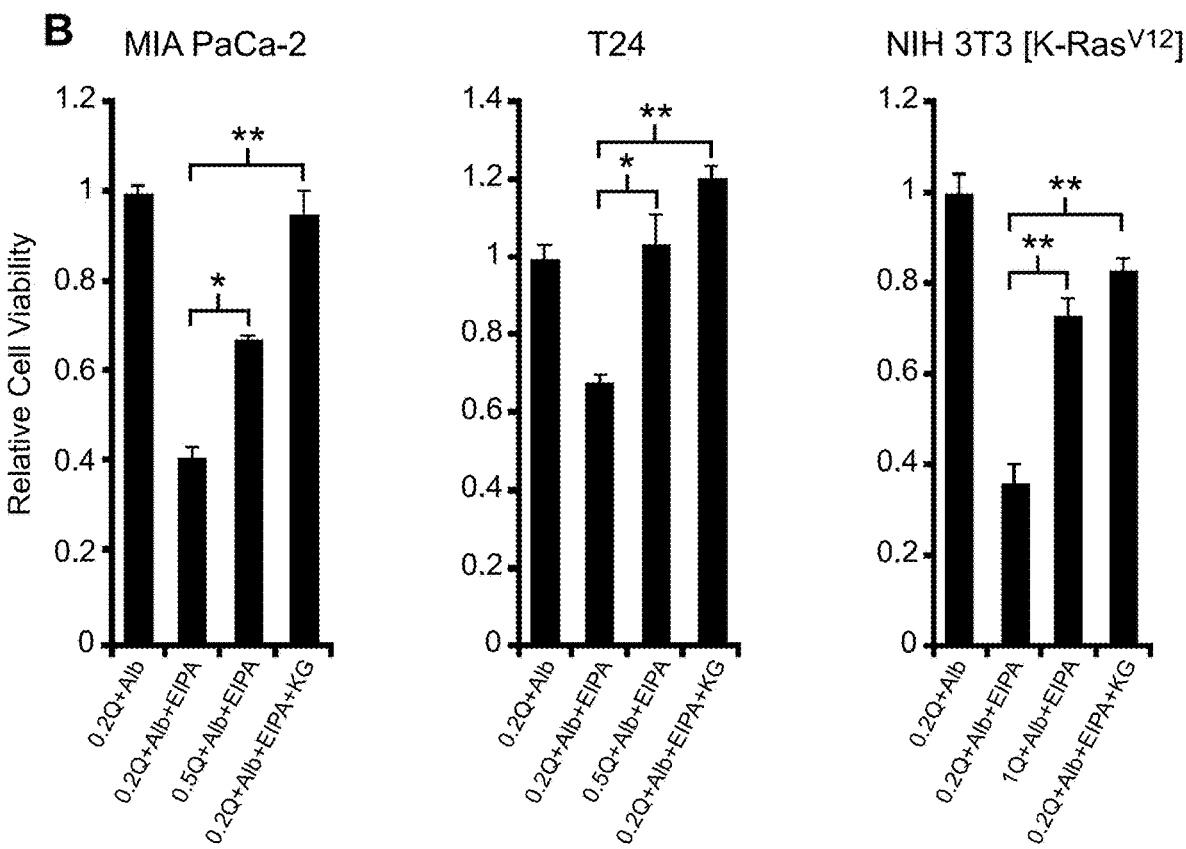
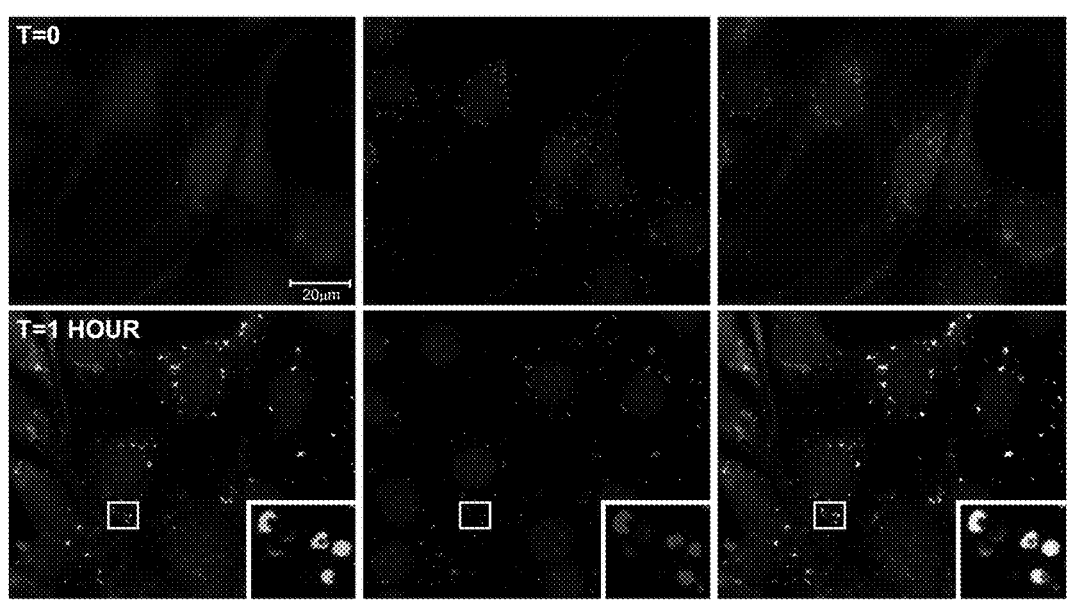

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial
<220> FEATURE:
<223> OTHER INFORMATION: Macropinocytosis targeting peptide

<400> SEQUENCE: 1
```

```
Arg Leu Arg Arg
1

<210> SEQ ID NO 2
<211> LENGTH: 10
<212> TYPE: PRT
<213> ORGANISM: Artificial
<220> FEATURE:
<223> OTHER INFORMATION: Macropinocytosis targeting peptide

<400> SEQUENCE: 2

Arg Arg Arg Gln Arg Arg Lys Lys Arg Gly
1               5                   10

<210> SEQ ID NO 3
<211> LENGTH: 9
<212> TYPE: PRT
<213> ORGANISM: Artificial
<220> FEATURE:
<223> OTHER INFORMATION: Macropinocytosis targeting peptide

<400> SEQUENCE: 3

Cys Ala Tyr His Arg Leu Arg Arg Cys
1               5
```

CANCER DIAGNOSTICS, THERAPEUTICS, AND DRUG DISCOVERY ASSOCIATED WITH MACROPINOCYTOSIS This application is a division of U.S. application Ser. No. 14/009,013, filed on Sep. 30, 2013, which is a national stage application under 35 U.S.C. § 371 of PCT Application No. PCT/US2012/031828, filed Apr. 2, 2012, which claims the priority benefit of U.S. Provisional Patent Application Ser. No. 61/470,945, filed Apr. 1, 2011, which is hereby incorporated by reference in its entirety.

This invention was made with government support under 2R01CA055360-19A1 awarded by the National Institutes of Health. The government has certain rights in the invention.

FIELD OF THE INVENTION

The present invention is directed to methods of diagnosing and treating cancer in a subject. A high-throughput method of identifying compounds suitable for treating a subject having cancer is also disclosed.

BACKGROUND OF THE INVENTION

Oncogenic mutations in Ras-encoding genes are found in approximately 30% of all tumors and are most prevalent in carcinomas of the pancreas, colon, lung and bladder. These mutations have profound effects on proliferation, cell survival and tumor invasion. Ras orchestrates these events by activating downstream effector pathways that regulate actin reorganization, gene expression and macropinocytosis.

Macropinocytosis is a stimulated form of fluid-phase uptake that involves extensive plasma membrane remodeling and the internalization of extracellular fluid via large endocytic structures called macropinosomes. Macropinocytosis plays a key role in various biological processes, including immune surveillance, nutrient uptake and pathogen infection. Interestingly, macropinocytosis is also stimulated in cells harboring oncogenic mutations; however, the functional significance of this stimulation is unknown.

The present invention is directed to overcoming these and other deficiencies in the art.

SUMMARY OF THE INVENTION

A first aspect of the present invention is directed to a method of inhibiting cancer cell proliferation and/or cancer cell survival. This method involves selecting cancer cells having enhanced macropinocytosis and administering to the selected cancer cells a macropinocytosis inhibitor under conditions effective to inhibit cancer cell proliferation and/or cell survival.

Another aspect of the present invention is directed to a method of treating a subject having cancer. This method involves selecting a subject having cancer, wherein the cancer is characterized by cancer cells having enhanced macropinocytosis and administering, to the selected subject, a macropinocytosis inhibitor under conditions effective to inhibit cancer cell proliferation and/or survival in the subject, thereby treating the subject having cancer.

Another aspect of the present invention is directed to a method of diagnosing cancer in a subject. This method involves administering to the cells of a subject a macropinocytosis marker and detecting the presence of the macropinocytosis marker in cells of the subject. The method further involves comparing the amount of macropinocytosis marker in cells of the subject to the amount of macropinocytosis marker in non-cancer cells and making a diagnosis of cancer in the subject based on said comparing.

Another aspect of the present invention is directed to a high-throughput method of identifying a cancer therapeutic. This method involves providing a population of cells having enhanced macropinocytosis and providing a macropinocytosis marker. The method further involves contacting the population of cells with a candidate compound under conditions effective for the candidate compound to inhibit macropinocytosis and detecting and comparing the uptake of the macropinocytosis marker in the presence and in the absence of the candidate compound. A decrease in marker uptake in the presence of the candidate compound compared to in the absence of the candidate compound identifies a cancer therapeutic The identification of new therapeutic strategies that offer significant improvement in clinical outcomes for oncogene-mediated cancers is urgently needed. Recent years have witnessed a renewed appreciation of the altered metabolic behavior of tumor cells and the critical role that such metabolic reprogramming plays in conferring growth and survival advantages to tumor cells. Of particular relevance, is the now widely accepted notion that cancer cells display a heightened state of dependency on glutamine, which they utilize as a substrate for various metabolic processes. The present invention defines a new mechanism that controls glutamine supply in cancer cells, and as such, will advance our understanding of the molecular pathways that account for the metabolic phenotype of oncogene-positive cancer cells. Furthermore, the present invention has identified new strategies for inhibiting cancer cell growth and survival via the targeting of tumor cell bioenergetics and macropinocytosis.

BRIEF DESCRIPTION OF THE DRAWINGS

FIG. 1A is a panel of fluorescent photomicrographs showing nuclear staining (DAPI), H-RAS$^{V12}$ expression, and macropinocytosis uptake (Dextran) in HeLa cells. The bottom right image shows an overlay of the nuclear, H-RAS$^{V12}$, and Dextran fluorescent localization. FIG. 1B is a bar graph showing quantification of macropinocytosis in HeLa cells as a function of H-RAS$^{V12}$ expression.

FIGS. 2A-2B are fluorescent photomicrographs showing macropinocytotic uptake in untransformed cells (vector; FIG. 2A) and cells genetically modified to express K-ras$^{V12}$ (FIG. 2B). FIG. 2C shows the quantitation of macropinocytotic uptake in both the control and K-ras$^{V12}$ cells.

FIG. 5C shows macropinocytosis positive cells within the tumors. FIG. 5B shows nuclear cell staining of the cells in FIG. 5C using DAPI. To distinguish between transplanted and host immune/stromal cells, the sections were counterstained with an epithelial-specific anti-cytokeratin antibody (FIG. 5D). An overlay of DAPI, dextran and cytokeratin staining is shown in FIG. 5E.

FIG. 6A is a panel of fluorescent photomicrographs showing nuclear cell staining (top, left), mutant H-Ras$^{V12}$ expression (top, right), protein uptake (FITC-BSA; bottom, left), and co-localization of the three (bottom, right). FIG. 6B shows the quantitation of protein uptake in oncogenic Ras$^{V12}$ expressing cells FIGS. 7A and 7B show albumin internalization and macropinocytosis, respectively in HeLa cells. Internalization of albumin into macropinosomes is shown in the overlay image of FIG. 7C.

FIG. 8A shows Lysotracker (Invitrogen) staining, which labels acidic compartments, in control HeLa cells not expressing oncogenic H-Ras$^{V12}$ (DOX) and HeLa cells expressing H-Ras$^{V12}$ (NO DOX). FIG. 8B shows the quantitation of Lysotracker staining.

FIGS. 9A and 9B left and right panels). Cells were pulsed with TMR-dextran (middle and right panels) and incubated with TMR-dextran-free media for 0-hours (FIG. 9A) and 6-hours (FIG. 9B)

FIG. 10A shows BSA-staining after 3 hours of chase. The intensity the intensity of the fluorescent signal that was incorporated into vesicular spots was quantified using automated spot detection (FIG. 10B).

FIG. 12A shows the finely controlled expression of oncogenic H-Ras$^{V12}$ in HeLa cells with decreasing concentrations of tetracycline. FIG. 12B is a graph showing the survival ratio of oncogenic Ras-expressing HeLa cells in the presence of decreasing amounts of tetracycline correlating to increasing levels of oncogene expression (50 ng/mL, 10 ng/mL, or 0 ng/mL of tetracycline) over 5 days.

FIGS. 16A-16D demonstrate BSA rescue of glutamine addiction in the T24 bladder cancer (FIGS. 16A-16B) and MIA-PaCa-2 pancreatic cancer cell lines (FIGS. 16C-16D) harboring oncogenic Ras mutations. FIGS. 16A and 16C show rescue of cell viability with higher extracellular albumin concentrations in the T24 and MIA-PaCa-2 cell lines, respectively. FIGS. 16B and 16D plot the survival advantage (a ratio of the viability of the high protein media cells to the low protein media cells) for the timepoints indicated.

FIGS. 20A-20C show the effects of albumin supplementation on cell growth. FIG. 20A shows intracellular levels of glutamate and α-ketoglutarate are elevated following the incubation of NIH 3T3 [K-RasV$^{12}$] cells in complete medium supplemented with 2% albumin ("CM+Alb") compared to complete medium alone ("CM"). Intracellular accumulation of both metabolites was blocked by 25 mM EIPA treatment ("CM+Alb+EIPA"). Data are expressed as arbitrary units and are presented relative to the values obtained for the CM condition. FIG. 20B shows that the effects of EIPA treatment (25 mM) are suppressed by increasing the glutamine levels in the growth media to the indicated concentrations (i.e., 0.5 Q indicates 0.5 mM glutamine) or the addition to the medium of 7 mM dimethyl α-ketoglutarate ("KG"), a cell-penetrant form of α-ketoglutarate. The concentrations of glutamine used represent the minimum concentration that is required to rescue the effects of EIPA for each cell line. Data are presented relative to the values obtained for the 0.2 Q+Alb condition. Error bars indicate mean +/− SEM for n=3 independent experiments. Statistical significance was determined via t-test; *p<0.05, **p<0.01. FIG. 20C shows the analysis of DQ-BSA fluorescence in NIH 3T3 [K-Ras$^{V12}$] cells that were co-incubated with DQ-BSA (green) and TMR-dextran (red) and fixed either immediately at the end of the incubation (T=0) or following a 1 hour chase in media free of both DQ-BSA and TMR-dextran (T=1 HOUR). The fluorescent signal emanating from DQ-BSA (T=1 HOUR) is an indication of albumin degradation. Insets represent a higher magnification of the boxed area. Images shown in are representative of at least 3 independent experiments.

DETAILED DESCRIPTION OF THE INVENTION

Figure 1A:
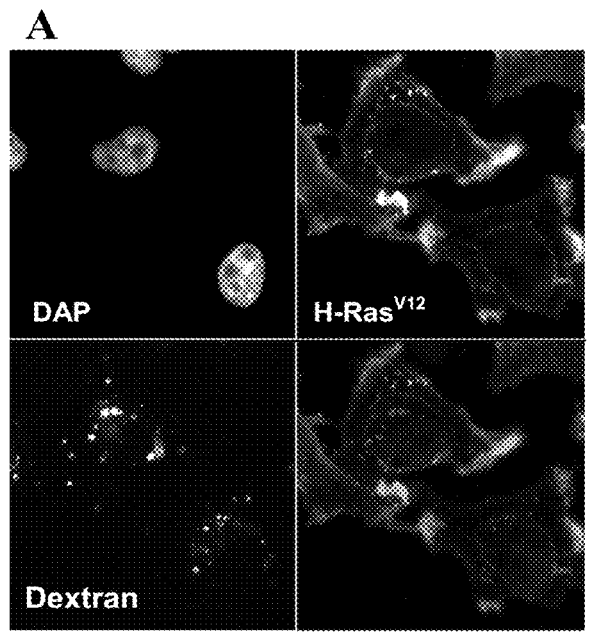
FIGS. 1A-1B show macropinocytosis in HeLa cells expressing oncogenic Ras$^{V12}$.

A first aspect of the present invention is directed to a method of inhibiting cancer cell proliferation and/or cancer cell survival. This method involves selecting cancer cells having enhanced macropinocytosis and administering to the selected cancer cells a macropinocytosis inhibitor under conditions effective to inhibit cancer cell proliferation and/or cell survival.

In accordance with this aspect of the present invention, the selected cells have enhanced macropinocytosis that is stimulated or mediated by the expression of an oncogene. Accordingly, a cell having enhanced macropinocytosis includes any cell having an activated oncogene. As used herein, "oncogene" is a gene that plays a normal role in the cell as a proto-oncogene, but has been altered by mutation and contributes to the growth of a tumor. Oncogenes are well known in the art and include, without limitation, c-Sis, epidermal growth factor receptor (EGFR), platelet-derived growth factor receptor (PDGFR), vascular endothelial growth factor receptor (VEGF), HER2/neu, Src-family of oncogenes, Syk-ZAP-70 family of tyrosine kinases, BTK family of tyrosine kinases, Abl, Raf kinase, cyclin-dependent kinases, Ras, myc, Wnt, and Trk. In one embodiment of the present invention, the selected cell expresses a ras oncogene, e.g., a mutant H-ras gene, mutant N-ras gene, or a mutant K-ras gene. In another embodiment of the invention, the selected cell expresses a v-src or a mutant c-src gene. In another embodiment of the invention, the selected cell expresses an oncogenic EGFR gene.

While oncogene-stimulated macropinocytosis has been previously demonstrated (see, e.g., Bar-Sagi et al., "Induction of Membrane Ruffling and Fluid-Phase Pinocytosis in Quiescent Fibroblasts by Ras Proteins," *Science* 233(4678): 1061-68 (1986), which is hereby incorporated by reference in its entirety), the selective advantage that enhanced macropinocytosis confers to the oncogenic cells has not been appreciated. As described herein, applicants have found that oncogenic cancer cells gain a survival advantage, measured by their metabolic activity, as a result of enhanced macropinocytosis. Enhanced macropinocytosis in oncogenic cells results in the increased internalization of extracellular protein, which is used as a nutrient source in cancer cells. The increased protein uptake in low glutamine concentrations, which is typical of the in vivo cancer cell environment, enhances cancer cell viability. Accordingly, inhibiting macropinocytosis in oncogenic cancer cells inhibits proliferation and survival of these cells, resulting in inhibition of tumor formation and growth.

In accordance with this aspect of the invention, a suitable macropinocytosis inhibitor is any macropinocytosis inhibitor known in the art. Suitable macropinocytosis inhibitors include, without limitation, phosphatidylinositol (PI) 3-kinase inhibitors, Rho GTPase inhibitors, actin polymerase inhibitors, PKC inhibitors, phospholipase C inhibitors, Na$^+$/H$^+$ exchange inhibitors, and Erk/Mek/p38 combination inhibitors.

Because of its strict requirement for actin, the most commonly used inhibitors of macropinocytosis are actin polymerase inhibitors such as cytochalasins, particularly cytochalasin D. Macropinocytosis is also highly dependent on the activity of phosphatidylinositol (PI) 3-kinase (PI3K) and the activity of the Rho family small GTPases, which regulate actin rearrangements. Inhibitors of PI 3-kinases, such as wortmannin and LY294002, and Rho GTPases, such as toxin B, are suitable inhibitors of macropinocytosis for use in the present invention. In addition amiloride and its analogues (e.g., 5-N-ethyl-N-isoproamiloride (EIPA), dimethyl amiloride (DMA)), which inhibit the Na$^+$/H$^+$ exchange, can also be used in the methods of the present invention to inhibit macropinocytosis in cells.

Several promising molecular approaches in targeting the process of macropinocytosis have emerged recently, which target ARF- and Rho-family GTPases. Overexpression of ARF6 locked in its GTP-bound form, dominant-negative forms of the Rho family GTPases, and the autoinhibitory domain of the Rac-dependent kinase PAK1, all result in an inhibition of macropinocytosis.

Additional specific inhibitors of macropinocytosis that are suitable for use in the methods of the present invention include, without limitation, 2-nitro-4-carboxyphenyl N,N-diphenylcarbamate (NCDC), hexodecylphosphocholine (HPC), U73122, and Rottlerin.

In one embodiment of the present invention, inhibition of cancer cell proliferation and/or cancer cell survival is carried out ex vivo. In an alternative embodiment of the invention, inhibition of cancer cell proliferation and/or survival is carried out in vivo.

In vivo inhibition of cancer cell proliferation and/or survival requires targeted delivery of the macropinocytosis inhibitor to the oncogenic cells to achieve selective inhibition of macropinocytosis in only these cells. Since macropinocytosis plays a key role in a number of biological processes, general or systemic inhibition of macropinocytosis is undesirable. Methods of targeting macropinocytosis inhibitor delivery are described infra.

Another aspect of the present invention is directed to a method of treating a subject having cancer. This method involves selecting a subject having cancer, wherein the cancer is characterized by cancer cells having enhanced macropinocytosis. The method further involves administering to the selected subject, a macropinocytosis inhibitor under conditions effective to inhibit cancer cell proliferation and/or survival in the subject, thereby treating the subject having cancer.

In accordance with this aspect of the present invention, a "subject" or "patient" includes any animal. Preferably, the subject is a mammal, more preferably, the subject is a human.

Subjects suitable for treatment in accordance with this aspect of the invention are those subjects having cancerous cells which exhibit enhanced macropinocytosis. Therefore, selecting a subject suitable for treatment in accordance with this aspect of the present invention may involve administering to cells of the subject a macropinocytosis marker, detecting the macropinocytosis marker in the cells of the subject, and comparing the amount of macropinocytosis marker in the cells of the subject compared to non-cancerous cells (e.g., non-cancerous cells of the subject). Methods of measuring the level of cellular macropinocytosis in a subject are described in more detail infra.

In one embodiment of the invention, the enhanced macropinocytosis is stimulated or mediated by an oncogene as described supra. In other words, suitable subjects for treatment in accordance with the methods of the present invention, include those subjects having an oncogene-mediated cancer condition. Cancers that typically have an oncogene component include, without limitation, pancreatic cancer, lung cancer, breast cancer, ovarian cancer, colorectal cancer, thyroid cancer, liver cancer, bladder cancer and leukemia.

Any of the macropinocytosis inhibitors described supra can be administered to the subject in accordance with this aspect of the present invention. In a preferred embodiment of the invention, the macropinocytosis inhibitor is targeted to cancer cells, thereby inhibiting macropinocytosis in cancer cells, but not in normal, non-cancerous cells. As noted above, systemic or general inhibition of macropinocytosis in an individual is not desired. To achieve selective inhibition of macropinocytosis in cancer cells only, the agent is administered directly to the site of the cancer cells (i.e., direct tumor injection). Alternatively, the macropinocytosis inhibitor is housed in a targeted delivery vehicle (suitable delivery vehicles are described infra). In yet another embodiment, selective targeting of the macropinocytosis inhibitor is achieved by coupling the inhibitor to a targeting ligand for directed delivery of the inhibitor.

In accordance with this aspect of the invention, ligand directed delivery of the inhibitor is achieved using a cancer cell specific ligand targeting strategy. Suitable ligand directed cancer cell targeting systems are known in the art and include, without limitation, Eph-ligand based delivery (see U.S. Patent Publication No. 2010/0240594 to Pellecchia et al., which is hereby incorporated by reference in its entirety), vasoactive intestinal peptide, somatostatin, gastrin releasing peptide, bombesin, or substance P ligand based delivery systems (see U.S. Patent Publication No. 2010/0184651 to Maithal et al., which is hereby incorporated by reference in its entirety), urokinase, urokinase A chain, epidermal growth factor (EGF), transforming growth factor-alpha (TGFα), insulin-like growth factor, interleukin-4 (IL-4), interleukin-6 (IL-6), platelet-derived growth factor (PDGF), fibroblast growth factor (FGF), laminin, vascular endothelial growth factor (VEGF), and annexin V ligand based delivery systems (see U.S. Patent Publication No. 2005/0036984 to Harrison et al., which is hereby incorporated by reference in its entirety). In addition, a ligand for nucleophosmin, HSC70, BIP, Grp75, PDI, PDI ER60 precursor, HSP60, TCP-1ε, ERp29, HSP27, vimentin, α-internexin, cytokeratin 8, β-actin, γ-actin, β-tubulin, nm23-H1, valosin containing protein, tumor protein D52-like 2, ASF-2, hnRNPK, hnRNPC, 24.1D5 antigen, hnRNPA/B, Eukaryotic Elongation Factor 1δ Isoform 2, AU-rich element RNA binding protein, Rad 23 homologue B, annexin I, prohibitin, ubiquilin 1, or thioredoxin peroxidase 4, which are all surface markers for neoplastic cells (see U.S. Patent Publication No. 2007/0122414 to Georges et al., which is hereby incorporated by reference in its entirety), can also be used to target delivery of a macropinocytosis inhibitor of the invention to cancer cells. Other cancer specific targeting peptides are disclosed by U.S. Patent Publication No. 2004/0102382 to Schughart et al., which is hereby incorporated by reference in its entirety.

To facilitate cellular uptake of the macropinocytosis inhibitor, the inhibitor can be further conjugated to a macropinocytosis targeting peptide or ligand. Suitable macropinocytosis targeting peptides include arginine-rich synthetic or natural protein transduction domains. Exemplary macropinocytosis targeting peptides include, without limitation RLRR (SEQ ID NO:1) and RRRQRRKKRG (HIV-TAT; SEQ ID NO:2). The macropinocytosis targeting peptide can be conjugated directly to the inhibitor or can be combined with the cancer-specific targeting ligand to form a targeting ligand that directs cancer cell specific uptake of the inhibitor. An exemplary targeting peptide having dual specificity is disclosed in Nishimura et al., "Combinatorial Targeting of the Macropinocytotic Pathway in Leukemia and Lymphoma Cells," *J. Biol. Chem.* 283(17):11752-62 (2008), which is hereby incorporated by reference in its entirety. This targeting peptide combines a lymph node homing motif (CAY) with an arginine-rich (RLRR) macropinocytosis motif to achieve selective uptake by leukemic/lymphoma cells. The resulting targeting peptide has a sequence of CAYHRLRRC (SEQ ID NO:3).

An alternative approach for promoting the cellular uptake of a macropinocytosis inhibitor of the present invention is the use of a cell penetrating peptide (CPP). CPPs translocate across the plasma membrane of eukaryotic cells by a seemingly energy-independent pathway and have been used successfully for intracellular delivery of macromolecules, including antibodies, peptides, proteins, and nucleic acids, with molecular weights several times greater than their own. Several commonly used CPPs, including polyarginines, transportant, protamine, maurocalcine, and M918, are suitable targeting moieties for use in the present invention and are well known in the art (see Stewart et al., "Cell-Penetrating Peptides as Delivery Vehicles for Biology and Medicine," *Organic Biomolecular Chem* 6:2242-2255 (2008), which is hereby incorporated by reference in its entirety). Additionally, methods of making CPP are described in U.S. Patent Application Publication No. 20080234183 to Hallbrink et al., which is hereby incorporated by reference in its entirety. The CPP can also be conjugated to a cancer-specific targeting ligand to achieve dual-targeting specificity.

Another suitable moiety useful for enhancing the cellular uptake of the macropinocytosis inhibitor is an "importation competent" signal peptide as disclosed by U.S. Pat. No. 6,043,339 to Lin et al., which is hereby incorporated by reference in its entirety. An importation competent signal peptide is generally about 10 to about 50 amino acid residues in length, typically hydrophobic residues, that renders the inhibitor capable of penetrating through the cell membrane from outside the cell to the interior of the cell. An exemplary importation competent signal peptide includes the signal peptide from Kaposi fibroblast growth factor (see U.S. Pat. No. 6,043,339 to Lin et al., which is hereby incorporated by reference in its entirety). Other suitable peptide sequences can be selected from the SIGPEP database (see von Heijne G., "SIGPEP: A Sequence Database for Secretory Signal Peptides," *Protein Seq. Data Anal.* 1(1):41-42 (1987), which is hereby incorporated by reference in its entirety). The importation competent signal peptide can further be coupled to the cancer-cell specific targeting ligand.

In accordance with the methods of the present invention, administering a macropinocytosis inhibitor to a subject can be carried out concurrently with other therapeutic approaches, i.e., the agent is administered as part of a combination therapy. Accordingly, in one embodiment of the invention, the agent is administered in combination with one or more additional cancer therapeutics such as, a chemotherapeutic, radiation (e.g., external beam radiation therapy or brachytherapy), an anti-angiogenic therapeutic, an anti-ras therapeutic, or an immune enhancing therapeutic.

Suitable chemotherapeutic agents for combination therapies include, without limitation, alkylating agents (e.g., chlorambucil, cyclophosphamide, CCNU, melphalan, procarbazine, thiotepa, BCNU, and busulfan), antimetabolites (e.g., methotraxate, 6-mercaptopurine, and 5-fluorouracil), anthracyclines (daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin) or plant alkaloids (e.g., topoisomerase inhibitors, vinca alkaloids, taxanes, and epipodophyllotoxins).

Anti-angiogenic therapeutics suitable for use in a combination therapy approach with a macropinocytosis inhibitor of the invention include, without limitation a vascular endothelial growth factor (VEGF) inhibitor, basic fibroblast growth factor (bFGF) inhibitor, vascular endothelial growth factor receptor (VEGFR) antagonist, platelet-derived growth factor receptor (PDGFR) antagonist, fibroblast growth factor receptor (FGFR) antagonist, Angiopoietin receptor (Tie-2) antagonist, epidermal growth factor receptor (EGFR, ErbB) antagonist, or any combination thereof. A number of suitable small molecule angiogenic inhibitors are known in the art or are under clinical development (see, e.g., Wu et al., "Anti-Angiogenic Therapeutic Drugs for the Treatment of Human Cancer," J. Cancer Molecules 4(2): 37-45 (2008), which is hereby incorporated by reference in its entirety). The angiogenic inhibitors include, without limitation, Gefitinib (an ErbB inhibitor), Lapatinib (a dual ErbB1/ErbB2 inhibitor), Erlotinib, Canertinib (a pan-ErbB inhibitor), Vatalanib (VEGF receptor inhibitor), Imatinib (multi-targeted inhibitor of Bcr-Abl, c-kit, and PDGF-R inhibitor), Sunitinib (multi-targeted inhibitor of VEGFR, PDGFR Kit, Flt3, Tet and CSF1R inhibitor), Sorafenib (multi-targeted inhibit of VEGFR and PDGFR), Pazopanib (a multi-targeted inhibitor of VEGFR-1, VEGFR-2, VEGFR-3, PDGF-α, PDGFR-β, and c-kit). Alternatively, the anti-vasculogenic therapeutic is a monoclonal antibody. Suitable antibody therapeutics include, without limitation, Bevacizumab (VEGF antibody), IMC-1C11 (VEGFR-2 antibody), mF4-31C1 (VEGFR-3 antibody), and Vitaxin (integrin $\alpha_v\beta_3$ antibody).

Other anti-angiogenic as well as anti-stromal agents suitable for use in a combination therapy comprising a macropinocytosis inhibitor of the present invention are disclosed in Bissell et al., "Why Don't We Get More Cancer? A Proposed Role of the Microenvironment in Restraining Cancer Progression," Nat. Med. 17(3):320-329 (2011), which is hereby incorporated by reference in its entirety.

Suitable anti-ras therapeutic agents for use in combination with a macropinocytosis inhibitor of the present invention include, without limitation, S-trans, transfarnesylthiosalicylic acid (FTS), a non-toxic, specific Ras antagonist (see Weisz et al., "A New Functional Ras Antagonist Inhibits Human Pancreatic Tumor Growth in Nude Mice," Oncogene 18(16):2579-2588 (1999), which is hereby incorporated by reference in its entirety), and the farnesyltransferase inhibitor, FTI-277, (see Bernhard et al., "The Farnesyltransferase Inhibitor FTI-277 Radiosensitizes H-ras-transformed Rat Embryo Fibroblasts," Cancer Research 56: 1727-1730 (1996), which is hereby incorporated by reference in its entirety).

In an alternative embodiment of the invention, the agent is administered as a part of an adjuvant therapy regime. In particular, this involves chemotherapy, hormone therapy, radiation therapy, immunotherapy, or a targeted therapy together with an agent that inhibits macropinocytosis prior to and/or after surgery.

Pharmaceutical compositions containing macropinocytosis inhibitors suitable for use in the methods of the present invention can include a pharmaceutically acceptable carrier, one or more active agents, and a suitable delivery vehicle. Suitable delivery vehicles include, but are not limited to viruses, bacteria, biodegradable microspheres, microparticles, nanoparticles, liposomes, collagen minipellets, and cochleates.

In one embodiment of the present invention, the delivery vehicle is a liposome delivery vehicle. Liposomes are vesicles comprised of one or more concentrically ordered lipid bilayers which encapsulate an aqueous phase. A liposome which includes macropinocytosis inhibitor is contacted with the target cancer cell under conditions effective for delivery of the inhibitory agent into the cancer cell. For administration to a primary tumor site, the liposomal vesicles need not be targeted to the cancer cells per se. However, where the cancer cells to be treated include metastatic cells and possible multiple secondary tumor sites, then it is desirable to administer liposomes that are targeted for delivery to the cancer cells per se. The liposome delivery system can be made to accumulate at a target organ, tissue, or cell via active targeting (e.g., by incorporating an antibody or other ligand on the surface of the liposomal vehicle). This can be achieved using antibodies or ligands specific for an appropriate cancer cell marker as described supra.

Different types of liposomes can be prepared according to Bangham et al.,"Diffusion of Univalent Ions across the Lamellae of Swollen Phospholipids," J. Mol. Biol. 13:238-252 (1965); U.S. Pat. No. 5,653,996 to Hsu et al.; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., each of which is hereby incorporated by reference in its entirety.

These liposomes can be produced such that they contain, in addition to the macropinocytosis inhibitor, other therapeutic agents, such as anti-inflammatory agents, chemotherapeutic agents, or immune-enhancing agents (e.g., IL-2 or interferon alpha or GM-CSF), which would also be released at the target site (e.g., Wolff et al., "The Use of Monoclonal AntiThy1-IgG1 for the Targeting of Liposomes to AKR-A Cells in vitro and in vivo," Biochem. Biophys. Acta 802:259 (1984), which is hereby incorporated by reference in its entirety).

In another embodiment of the present invention, the delivery vehicle is a viral vector. Viral vectors are particularly suitable for the delivery of inhibitory nucleic acid molecules, such as siRNA or shRNA molecules (e.g., when targeting ARF and/or Rho family of GTP-ases). Suitable gene therapy vectors include, without limitation, adenoviral vectors, adeno-associated viral vectors, retroviral vectors, lentiviral vectors, and herpes viral vectors.

Adenoviral viral vector delivery vehicles can be readily prepared and utilized as described in Berkner, "Development of Adenovirus Vectors for the Expression of Heterologous Genes," Biotechniques 6:616-627 (1988) and Rosenfeld et al., "Adenovirus-Mediated Transfer of a Recombinant Alpha 1-Antitrypsin Gene to the Lung Epithelium In Vivo," Science 252:431-434 (1991), WO 93/07283 to Curiel et al., WO 93/06223 to Perricaudet et al., and WO 93/07282 to Curiel et al., which are hereby incorporated by reference in their entirety. Adeno-associated viral delivery vehicles can be constructed and used to deliver an inhibitory nucleic acid molecule of the present invention to cells as described in Shi et al., "Therapeutic Expression of an Anti-Death Receptor-5 Single-Chain Fixed Variable Region Prevents Tumor Growth in Mice," Cancer Res. 66:11946-53 (2006); Fukuchi et al., "Anti-Aβ Single-Chain Antibody Delivery via Adeno-Associated Virus for Treatment of Alzheimer's Disease," Neurobiol. Dis. 23:502-511 (2006); Chatterjee et al., "Dual-Target Inhibition of HIV-1 In Vitro by Means of an Adeno-Associated Virus Antisense Vector,"

Science 258:1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179:733-738 (1994); and Zhou et al., "Adeno-associated Virus 2-Mediated Transduction and Erythroid Cell-Specific Expression of a Human Beta-Globin Gene," *Gene Ther.* 3:223-229 (1996), which are hereby incorporated by reference in their entirety. In vivo use of these vehicles is described in Flotte et al., "Stable in Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver a nucleic acid molecule to a target cell. One such type of retroviral vector is disclosed in U.S. Pat. No. 5,849,586 to Kriegler et al., which is hereby incorporated by reference. Other nucleic acid delivery vehicles suitable for use in the present invention include those disclosed in U.S. Patent Publication No. 20070219118 to Lu et al., which is hereby incorporated by reference in its entirety.

Viral vectors are administered to a subject by, for example, intravenous injection, local administration (U.S. Pat. No. 5,328,470 to Nabel et al., which is hereby incorporated by reference in its entirety) or by stereotactic injection (see e.g., Chen et al., "Gene Therapy for Brain Tumors: Regression of Experimental Gliomas by Adenovirus Mediated Gene Transfer In Vivo," *Proc. Nat'l. Acad. Sci. USA* 91:3054-3057 (1994), which is hereby incorporated by reference in its entirety). The pharmaceutical preparation of the gene therapy vector can include the gene therapy vector in an acceptable diluent, or can comprise a slow release matrix in which the gene delivery vehicle is imbedded.

As an alternative to viral-vector delivery, nucleic acid molecule macropinocytosis inhibitors (e.g., siRNA molecule) are encapsulated in a lipid formulation to form a nucleic acid-lipid particle as described in Semple et al., "Rational Design of Cationic Lipids for siRNA Delivery," *Nature Biotech.* 28:172-176 (2010) and WO2011/034798 to Bumcrot et al., WO2009/111658 to Bumcrot et al., and WO2010/105209 to Bumcrot et al., which are hereby incorporated by reference in their entirety.

In another embodiment of the present invention, the delivery vehicle is a nanoparticle. A variety of nanoparticle delivery vehicles are known in the art and are suitable for delivery of a macropinocytosis inhibitor of the invention (see e.g., van Vlerken et al., "Multi-functional Polymeric Nanoparticles for Tumour-Targeted Drug Delivery," *Expert Opin. Drug Deliv.* 3(2):205-216 (2006), which is hereby incorporated by reference in its entirety). Suitable nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly(ethylene glycol) copolymers (Park et al., "Degradable Polyethylenimine-alt-Poly(ethylene glycol) Copolymers As Novel Gene Carriers," *J. Control Release* 105(3):367-80 (2005) and Park et al., "Intratumoral Administration of Anti-KITENIN shRNA-Loaded PEI-alt-PEG Nanoparticles Suppressed Colon Carcinoma Established Subcutaneously in Mice," *J Nanosci. Nanotechnology* 10(5):3280-3 (2010), which are hereby incorporated by reference in their entirety), liposome-entrapped siRNA nanoparticles (Kenny et al., "Novel Multifunctional Nanoparticle Mediates siRNA Tumor Delivery, Visualization and Therapeutic Tumor Reduction In Vivo," *J. Control Release* 149(2): 111-116 (2011), which is hereby incorporated by reference in its entirety). Other nanoparticle delivery vehicles suitable for use in the present invention include microcapsule nanotube devices disclosed in U.S. Patent Publication No. 2010/0215724 to Prakash et al., which is hereby incorporated by reference in its entirety.

In practicing the methods of the present invention, the administering step is carried out to achieve cancer cell specific inhibition of macropinocytosis, and such administration can be carried out systemically or via direct or local administration, i.e., to a tumor site. By way of example, suitable modes of systemic administration include, without limitation, orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes. Suitable modes of local administration include, without limitation, catheterization, implantation, direct injection, dermal/transdermal application, stenting, ear/eye drops, or portal vein administration to relevant tissues, or any other local administration technique, method or procedure, as is generally known in the art.

The agents of the present invention may be orally administered, for example, with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

When the macropinocytosis inhibitors of the present invention are administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices. Such devices allow continuous infusion of desired compounds avoiding multiple injections and multiple manipulations.

Compositions containing macropinocytosis inhibitors may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt Effective doses of the compositions of the present invention, for the treatment of cancer vary depending upon many different factors, including type and stage of cancer, means of administration, target site, physiological state of the patient, other medications or therapies administered, and physical state of the patient relative to other medical complications. Treatment dosages need to be titrated to optimize safety and efficacy.

Another aspect of the present invention is directed to a method of diagnosing cancer in a subject. This method involves administering to the cells of a subject a macropinocytosis marker and detecting the presence of the macropinocytosis marker in cells of the subject. The method further involves comparing the amount of macropinocytosis marker in cells of the subject to the amount of macropinocytosis marker in non-cancer cells and making a diagnosis of cancer in the subject based on this comparison.

In accordance with this aspect of the invention, an increase in the amount of macropinocytosis marker in cells of the subject compared to non-cancer cells indicates the subject has cancer. In a preferred embodiment of the present invention, a subject diagnosed with having cancer is treated with a macropinocytosis inhibitor in accordance with the methods of the present invention.

This diagnostic method of the invention can be carried out using cells obtained from the subject ex vivo or by direct administration of the labeled macropinocytosis marker to the subject in vivo as described below.

In accordance with this aspect of the present invention, an oncogene mediated cancer can be diagnosed. For example, any cancer involving an oncogenic ras, v-src, or oncogenic EGFR can be diagnosed. Suitable cancers for diagnosis include, without limitation, pancreatic cancer, lung cancer, colorectal cancer, thyroid cancer, liver cancer, bladder cancer, and leukemia.

Suitable macropinocytosis markers are biomolecules that are taken up via macropinocytosis, such as dextran, arginine rich peptides, peptides, and proteins (e.g., albumin). The macropinocytosis marker can further comprise a macropinocytosis targeting motif as described supra (e.g., an arginine-rich amino acid sequence). The macropinocytosis marker can be labeled with a radioisotope, fluorescent label, bioluminescent label or other label that is suitable for ex vivo and in vivo detection methods.

In one embodiment, the macropinocytosis inhibitor is radiolabeled. Suitable radioactive labels include $^{125}$I, $^{131}$I, $^{111}$In, or $^{99}$TC. Methods of radiolabeling targeting components, are known in the art and described in U.S. Pat. No. 5,514,363 to Shochat et al., which is hereby incorporated by reference in its entirety. Radioactivity is detected and quantified using a scintillation counter or autoradiography.

In another embodiment of the invention, the macropinocytosis marker is labeled with a fluorescent label. Exemplary fluorescent labels include chelates (europium chelates), fluorescein and its derivatives, rhodamine and its derivatives, dansyl, Lissamine, phycoerythrin and Texas Red. The fluorescent labels can be conjugated to the macropinocytosis marker using the techniques disclosed in CURRENT PROTOCOLS IN IMMUNOLOGY (Coligen et al. eds., 1991), which is hereby incorporated by reference in its entirety. Fluorescence can be detected and quantified using a fluorometer.

Exemplary bioluminescent labels include, without limitation, obelin (Matveev et al., "Genetically Engineered Obelin as a Bioluminescent Label in an Assay for a Peptide," *Anal. Biochem.* 270(1):69-74 (1999), which is hereby incorporated by reference in its entirety), liposomal aequorin (Ho et al., "Application of a Liposomal Bioluminescent Label in the Development of a Flow Injection Immunoanalytical System," *Anal. Chem.* 77(11): 3431-36 (2005), which is hereby incorporated by reference in its entirety), and Aqualite® (Smith et al., "Aqualite, a Bioluminescent Label for Immunoassay and Nucleic Acid Detection: Quantitative Analyses at the Attomol Level," *Proc. SPIE* 2680:156-66 (1996), which is hereby incorporated by reference in its entirety).

As mentioned above, the diagnostic method of the present invention can be carried out by direct administration of the labeled marker to a subject in vivo. This involves administering (for example, parenterally, subcutaneously, or intraperitoneally) the labeled macropinocytosis marker to the subject, permitting the labeled molecule to be taken up via the macropinocytotic mechanism, allowing clearance of labeled marker not taken up by macropinocytosis, and detecting the amount or level of labeled marker in the subject after a suitable time interval following the administration. The detected amount is then compared to the level of labeled marker taken up by non-cancer cells. This comparison can be made to the uptake of the marker by the same cells of the subject assessed at an early timepoint (i.e., a previous test) or to cells of the subject known to be healthy, cancer free cells.

The background level of macropinocytosis in a subject can be determined by various methods including, comparing the amount of labeled molecule detected to a standard value previously determined for a particular system. The size of the subject and the imaging system used will determine the quantity of imaging moiety needed to produce diagnostic images.

In the case of a radioisotope moiety, for a human subject, the quantity of radioactivity injected will normally range from about 5 to 20 millicuries of $^{99}$Tc. The labeled marker will then preferentially accumulate within cells having enhanced macropinocytosis. In vivo imaging is described in Burchiel et al., *Immunopharmacokinetics of Radiolabeled Antibodies and Their Fragments*, IN TUMOR IMAGING: THE RADIOCHEMICAL DETECTION OF CANCER (Burchiel et al. eds., 1982), which is hereby incorporated by reference in its entirety.

Depending on several variables, including the type of label used and the mode of administration, the time interval following the administration for permitting the labeled molecule to preferentially concentrate at sites in the subject and for unbound labeled molecule to be cleared to background level is 6 to 48 hours, 6 to 24 hours, or 6 to 12 hours. In another embodiment the time interval following administration is 5 to 20 days or 5 to 10 days.

The presence of the labeled molecule can be detected in the patient using methods known in the art for in vivo scanning and imaging of the body. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography. In one embodiment, the macropinocytosis marker is labeled with a radioisotope and is detected in the patient using a radiation responsive surgical instrument (U.S. Pat. No. 5,441,050 to Thurston et al., which is hereby incorporated by reference in its entirety). In another embodiment, the macropinocytosis marker is labeled with a fluorescent compound and is detected in the patient using a fluorescence responsive scanning instrument. In another embodiment, the macropinocytosis marker is labeled with a positron emitting metal and is detected in the patient using positron emission-tomography. In yet another embodiment, the macropinocytosis marker is labeled with a paramagnetic label and is detected in a patient using magnetic resonance imaging (MRI).

In one embodiment, monitoring the status of the cancer can be carried out by repeating the method for diagnosing the presence of cancer, for example, one month after initial diagnosis, six months after initial diagnosis, one year after initial diagnosis, etc. Monitoring the status of the cancer is particularly suitable when determining the responsiveness of a tumor to a particular course of therapeutic treatment.

Another aspect of the present invention is directed to a high-throughput method of identifying a cancer therapeutic. This method involves providing a population of cancer cells having enhanced macropinocytosis and providing a macropinocytosis marker. The method further involves contacting the population of cells with a candidate compound under conditions effective for the candidate compound to inhibit macropinocytosis and detecting and comparing the macropinocytotic uptake of the macropinocytosis marker in the presence and in the absence of the candidate compound. A decrease in marker uptake in the presence of the candidate compound compared to in the absence of the candidate compound identifies a cancer therapeutic. A detailed description of this aspect of the invention is described in Example 6 below.

In accordance with this aspect of the invention, the population of cells having enhanced macropinocytosis comprise an oncogene. In one embodiment of the invention, the population of cells comprise an oncogenic ras, src, or EGFR gene.

Suitable macropinocytosis markers and labels for the markers are described supra.

EXAMPLES

Figure 1B:
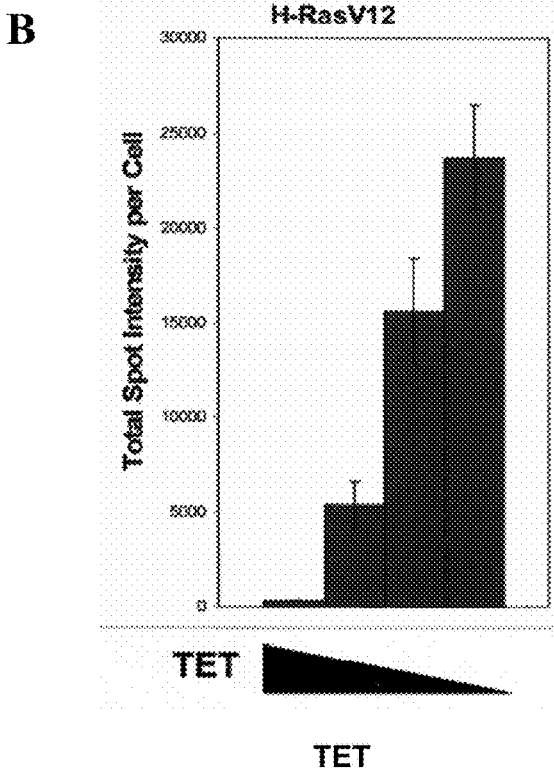

The following examples are provided to illustrate embodiments of the present invention but they are by no means intended to limit its scope Example 1—Macropinocytosis in Oncogenic Ras Cells The detection of stimulated fluid-phase macropinocytosis in human cells can be monitored using conventional fluorescent microscopy via the uptake of fluorescent 70 kDa dextran (FITC-dextran), a marker of macropinocytosis. In cells expressing an oncogenic form of Ras (Ras$^{V12}$), uptake of fluorescent dextran is apparent within several minutes and is dramatically increased compared to control cells (FIG. 1A). For the quantification of macropinocytosis, an intensity-based read-out assay that is described herein was used. This involves monitoring the uptake of FITC-dextran in HeLa cells that have been genetically modified to conditionally express H-Ras$^{V12}$ (Sparmann et al., "Ras-Induced Iinterleukin-8 Expression Plays a Critical Role in Tumor Growth and Angiogenesis," *Cancer Cell* 6(5):447-58 (2004), which is hereby incorporated by reference in its entirety). Quantification of macropinosomes in oncogenic Ras$^{V12}$-expressing cells indicates an approximate 30-fold increase when compared to uninduced control cells (FIG. 1B).

Figures 2A, 2B, 2C:
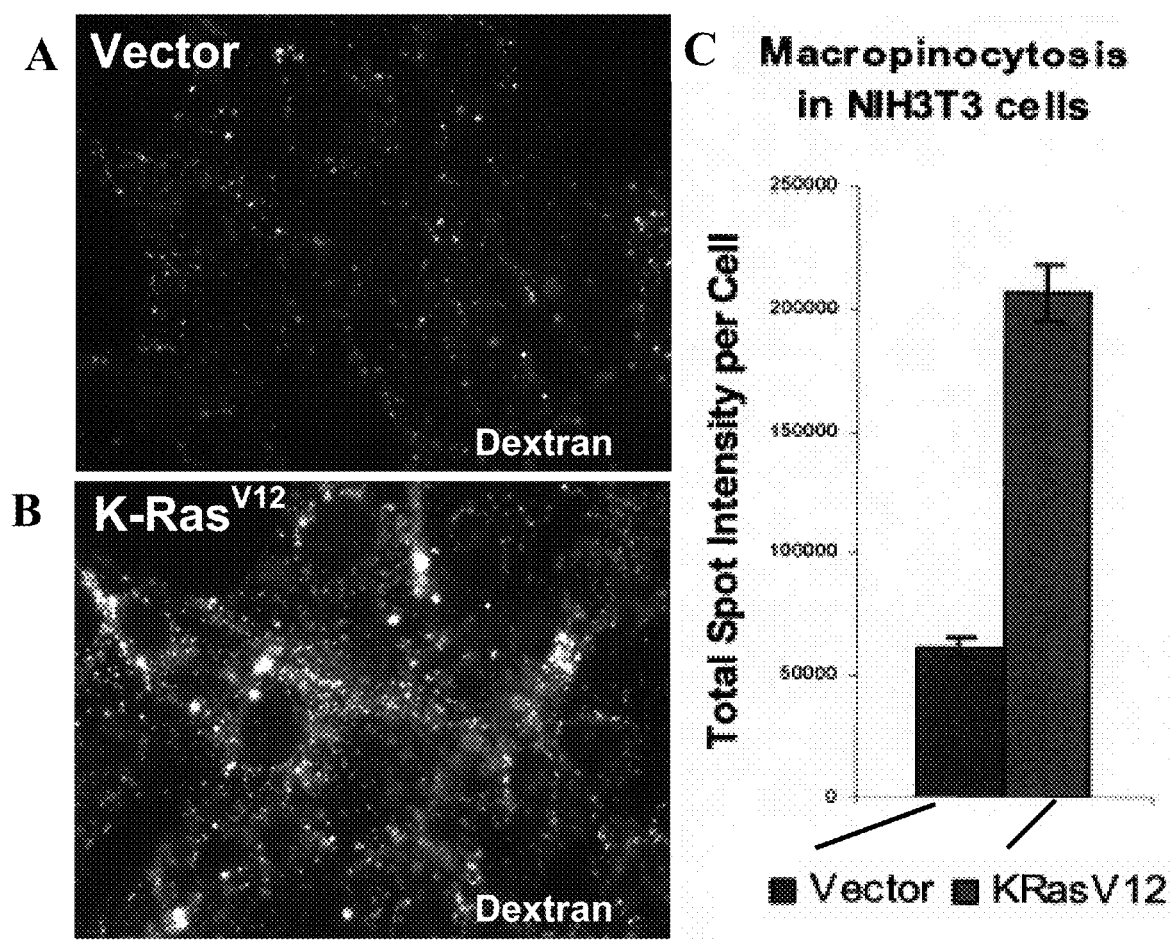
FIGS. 2A-2C show macropinocytosis in NIH 3T3 cells transformed by oncogenic Ras$^{V12}$.

As an extension to these findings, macropinocytosis in murine immortalized fibroblast cells was analyzed. Untransformed NIH3T3 cells display low levels of macropinocytosis, compared to Ras$^{V12}$-transformed cells (FIG. 2A). Using an amended protocol, fluid-phase uptake in these cells was quantified. K-Ras$^{V12}$-expressing cells have a 3-4 fold increase in macropinocytosis (FIG. 2B).

Example 2—Macropinocytosis in Oncogenic Cancer Cells

Figures 3A, 3B, 3C, 3D, 3E:
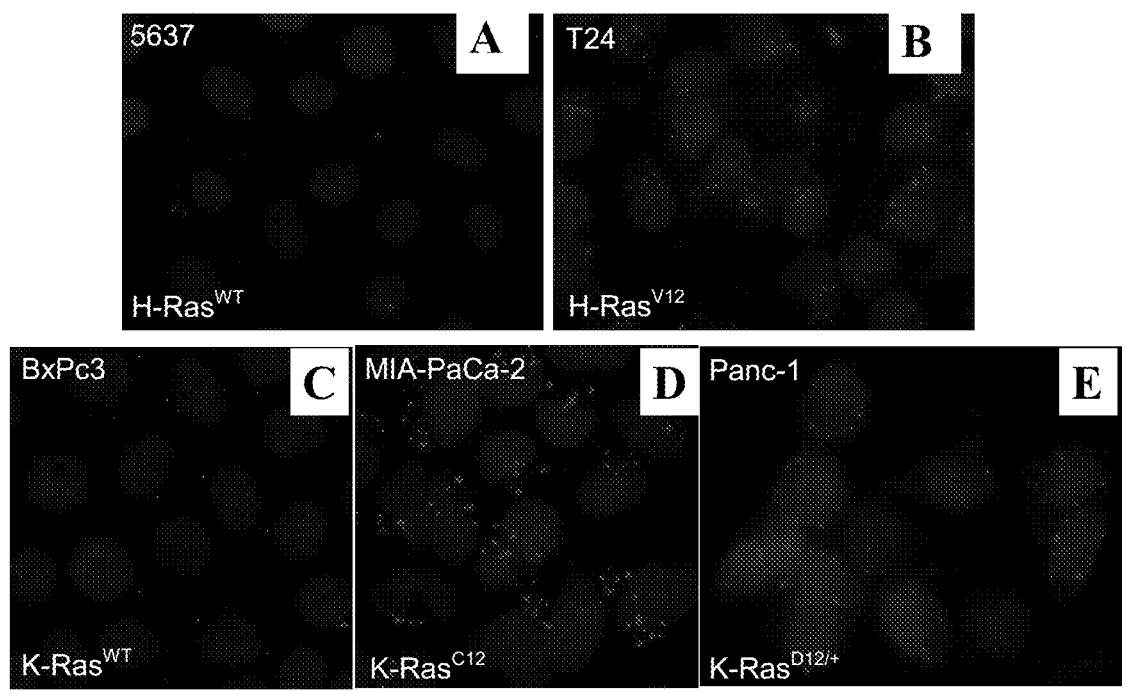
FIGS. 3A-3E show macropinocytosis in bladder (FIGS. 3A-3B) and pancreatic cancer cells (FIGS. 3C-3D), harboring oncogenic ras mutations (FIGS. 3B, 3D, and 3E). Macropinocytosis in bladder and pancreatic cells having a non-mutant ras gene is shown in FIGS. 3A and 3C, respectively.

It was postulated that cancer cells harboring oncogenic Ras mutations would display higher levels of macropinocytosis compared to cancer cells having a non-mutant Ras. For pancreatic cancer cells, macropinocytosis was analyzed in MIA-Paca-2 cells, which are homozygous for the oncogenic K-Ras$^{G12C}$ allele (Lopez-Crapez et al., "Rapid and Large-Scale Method to Detect K-Ras Gene Mutations in Tumor Samples," *Clin. Chem.* 43(6 Pt 1):936-42 (1997) and Pretlow et al., "K-Ras Mutations in Putative Preneoplastic Lesions in Human Colon," *J. Natl. Cancer Inst.* 85(24): 2004-7 (1993), which are hereby incorporated by reference in their entirety) and BxPc-3 cells that only express wild-type K-Ras (Aoki et al., "Liposome-Mediated in vivo Gene Transfer of Antisense K-Ras Construct Inhibits Pancreatic Tumor Dissemination in the Murine Peritoneal Cavity," *Cancer Res.* 55(17):3810-6 (1995), which is hereby incorporated by reference in its entirety). As a bladder model, uptake in T24 and 5637 cells was analyzed. T24 cells are homozygous for the oncogenic H-Ras$^{V12C}$ allele and 5637 cells only express wild-type H-Ras. Macropinosomes were visualized based on their ability to incorporate from the extracellular medium a tetramethylrhodamine-labeled 70 kDa dextran (TMR-dextran), an established marker of macropinocytosis (Kerr et al., "Defining Macropinocytosis," *Traffic* 10(4):364-71 (2009), which is hereby incorporated by reference in its entirety). The data indicates that macropinocytosis in MIA-Paca-2 (FIGS. 3D and 3E) and T24 cells (FIG. 3B) is appreciably higher compared to wild-type Ras cells (FIGS. 3A and 3C). TMR-dextran labeling in MIA-Paca-2 and T24 cells reflects uptake via macropinocytosis because it was inhibited by treatment with the amiloride analog EIPA, a macropinocytosis inhibitor that functions by inhibiting $Na^+/H^+$ exchange (Ivanov, "Pharmacological Inhibition of Endocytic Pathways: Is it Specific Enough to be Useful?" *Methods Mol. Biol.* 440:15-33 (2008), which is hereby incorporated by reference in its entirety). These results suggest that Ras-transformed cancer cells of display stimulated macropinocytosis.

Figures 4A, 4B, 4C, 4D:
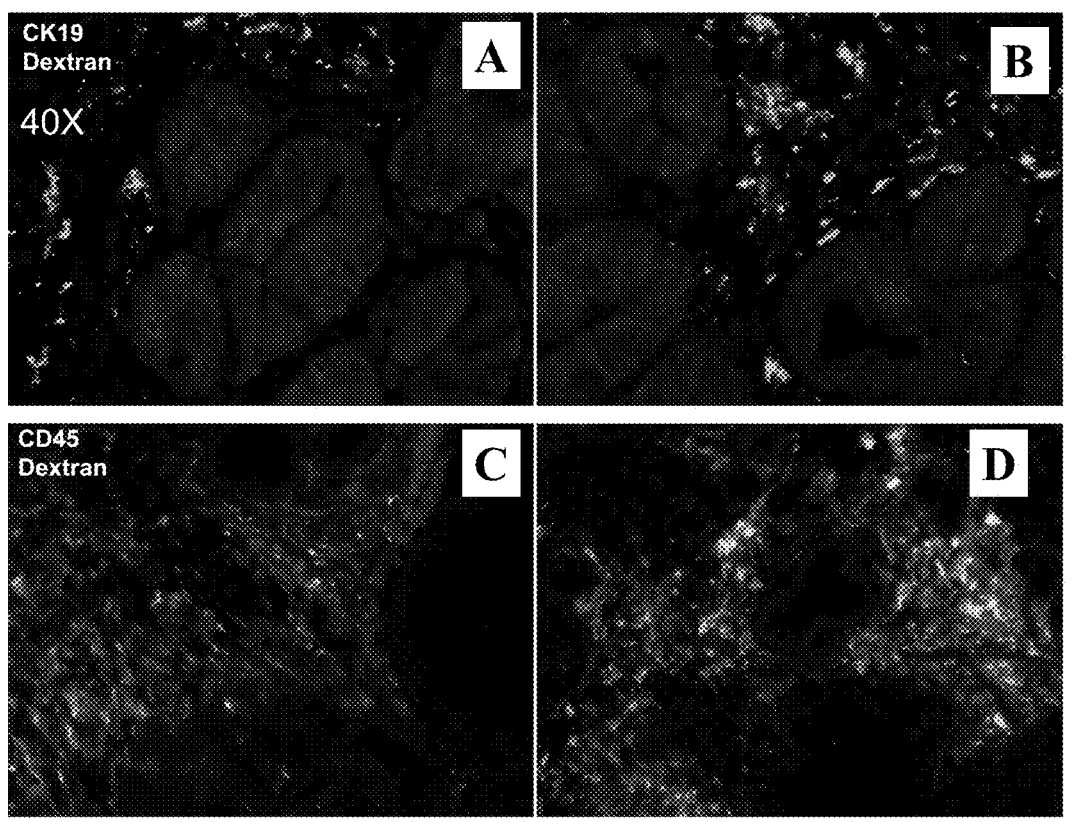
FIGS. 4A-4D are fluorescent photomicrographs shows macropinocytosis (Dextran) in CD45$^+$ immune cells (FIGS. 4C-4D) recruited to pre-cancerous lesions in p48-Cre; LSL-KRasG12D mice. The sections shown in FIGS. 4A and 4B are co-labeled with CK19, a marker of pancreatic duct cells and FITC-labeled dextran.

To determine the extent of stimulated macropinocytosis in a setting of endogenous tumors, p48-Cre;LSL-KRas$^{G12D}$ mice were utilized. These mice gradually develop pancreatic intraepithelial neoplasias (PanINs) that infrequently progress to invasive pancreatic ductal adenocarcinoma (PDA) (Hingorani et al., "Preinvasive and Invasive Ductal Pancreatic Cancer and its Early Detection in the Mouse," *Cancer Cell* 4(6): 437-50 (2003), which is hereby incorporated by reference in its entirety). In initial studies, these mice were injected at two months of age with 2 mg FITC-dextran, and pancreata were harvested two hours post-injection. As a control, pancreatic tissue from wild-type mice was also analyzed. Frozen sections from sectioned pancreata were analyzed using standard microscopic techniques and macropinocytosis-positive cells were identified by the visualization of FITC-positive puncta. There was an increase in the number of macropinocytosis-positive cells in pancreatic tissue expressing oncogenic K-Ras, compared to wild-type. To control for organ specificity, tissue originating from the liver, duodenum, and colon was analyzed and no appreciable uptake of the macropinocytosis marker in either wild-type or mutant tissue was observed. The identity of the cells using immunostaining various cell markers indicates that the macropinocytosis-positive cells in this particular cancer model are immune in origin as indicated by their CD45 positivity (FIGS. 4C-4D).

This dramatic display of macropinocytosis has clear diagnostic implications as described supra. Early pancreatic lesions can be detected by measuring the extent of macropinocytosis positivity within an organ. The number of macropinocytosis-positive immune cells corresponds to the progression of PanIN lesions as their frequency is higher in older animals (ranging from 1-7 months) that exhibit an age-dependent increase in the number and stage of lesions documented (Deramaudt et al., "Mutant KRAS in the Initiation of Pancreatic Cancer," *Biochim. Biophys. Acta.* 1756 (2):97-101 (2005), which is hereby incorporated by reference in its entirety).

Figures 5A, 5B, 5C, 5D, 5E:
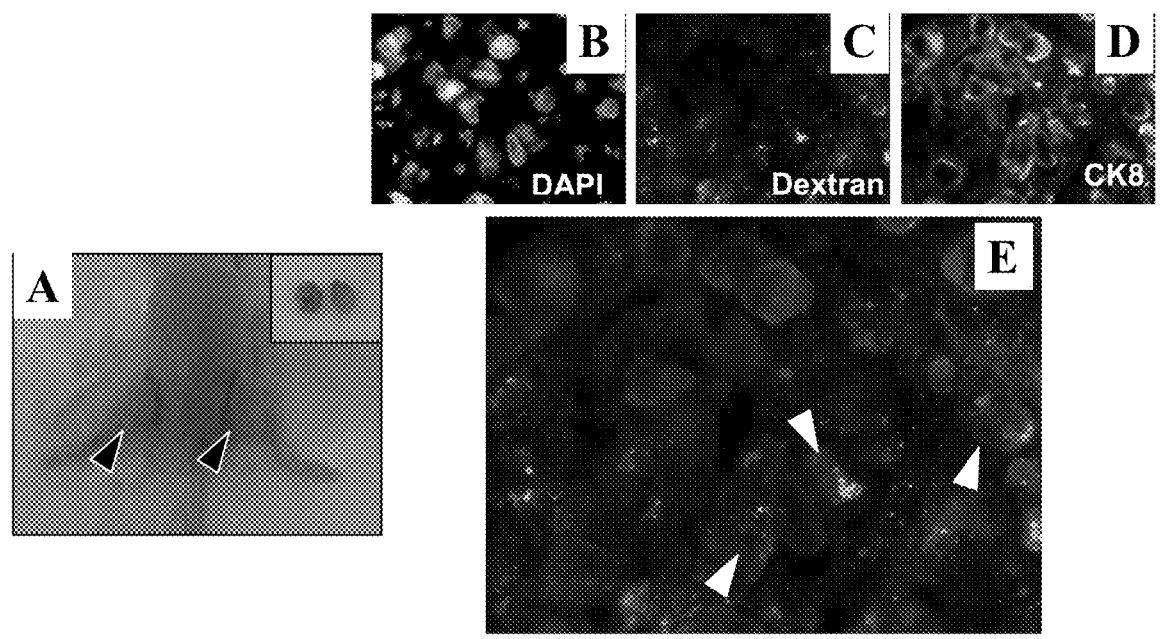
FIGS. 5A-5E show macropinocytosis in heterotopic xenograft tumors derived from human MIA-PaCa-2 pancreatic cancer cells. For the xenograft model, 1×10$^6$ pancreatic cancer cells (MIA-PaCa-2) were injected subcutaneously into the flanks of nude mice (FIG. 5A) and macropinocytosis by the tumor cells was analyzed three weeks post injection. To detect macropinocytosis, mice were intratumorally injected with fluorescently-labeled fluid-phase marker (FITC-dextran) at 2 mg/g.

Example 3—Macropinocytosis in Heterotopic Xenograft Tumors Derived from Human MIA-PaCa-2 Pancreatic Cancer Cells To establish the in vivo prevalence of macropinocytosis in pancreatic cancer, an experimental xenograft mouse model was employed. For the xenograft model, $1 \times 10^6$ pancreatic cancer cells (MIA-PaCa-2) were injected subcutaneously into the flanks of nude mice (FIG. 5A). Macropinocytosis by the tumor cells was analyzed at 3 weeks post-injection, when the tumors attained an average volume of 300-500 mm³. To detect macropinocytosis in tumor cells, mice were intratumorally injected with a fluorescently-labeled fluid-phase marker (FITC-dextran) at 2 mg/g. The presence of macropinocytosis-positive cells within the tumors was assessed by the microscopic visualization of FITC-positive puncta in frozen sections (FIGS. 5C and 5E; cell nuclear localization is shown using DAPI in FIGS. 5B and 5E). To distinguish between transplanted and host immune/stromal cells, the sections were counterstained with an epithelial-specific anti-cytokeratin antibody (FIGS. 5D and 5E).

Example 4—Protein Uptake in Oncogenic Ras Cells

Figure 6A:
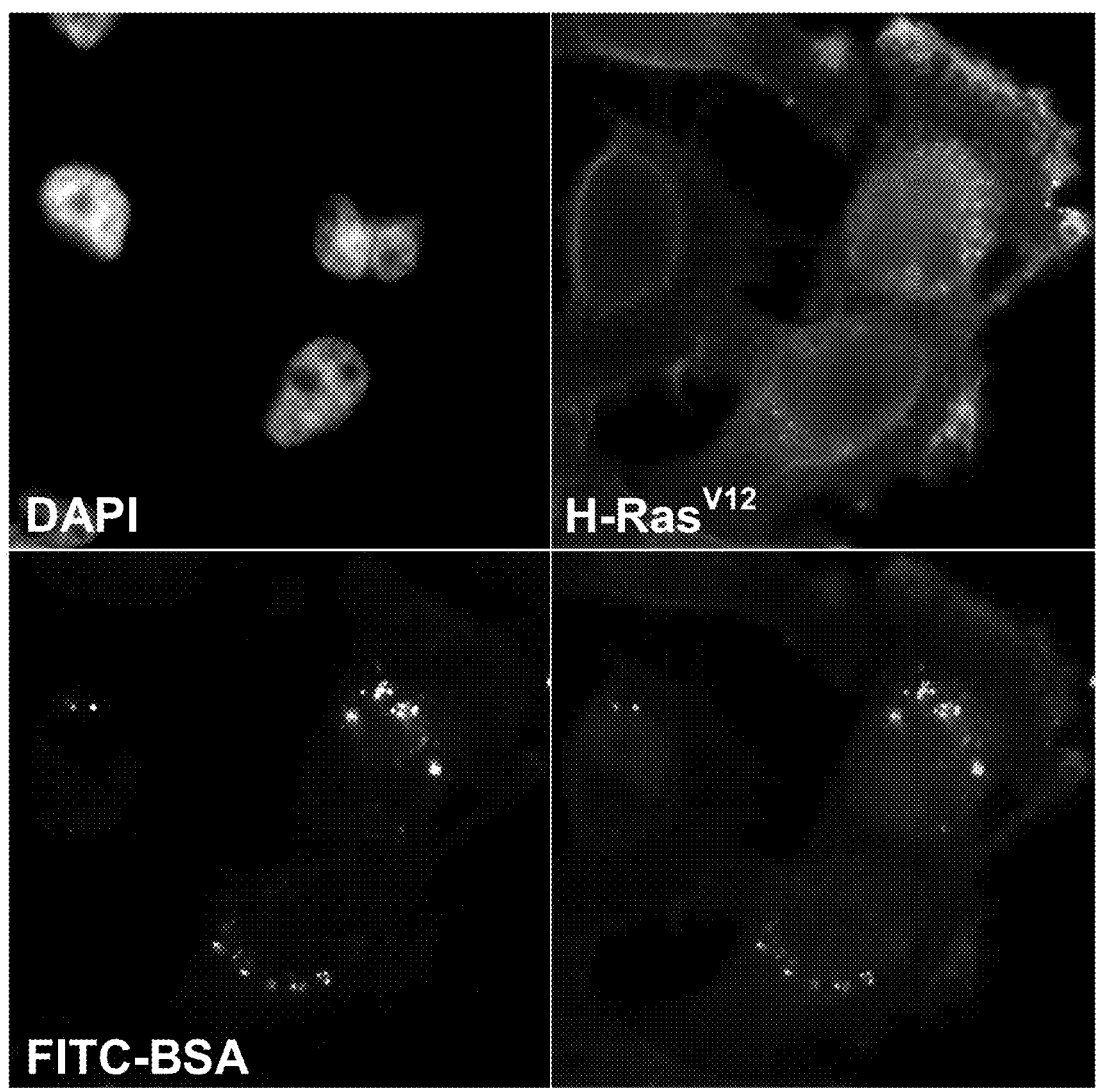
FIGS. 6A-6B show protein uptake in HeLa cells expressing oncogenic Ras$^{V12}$.
Figure 6B:
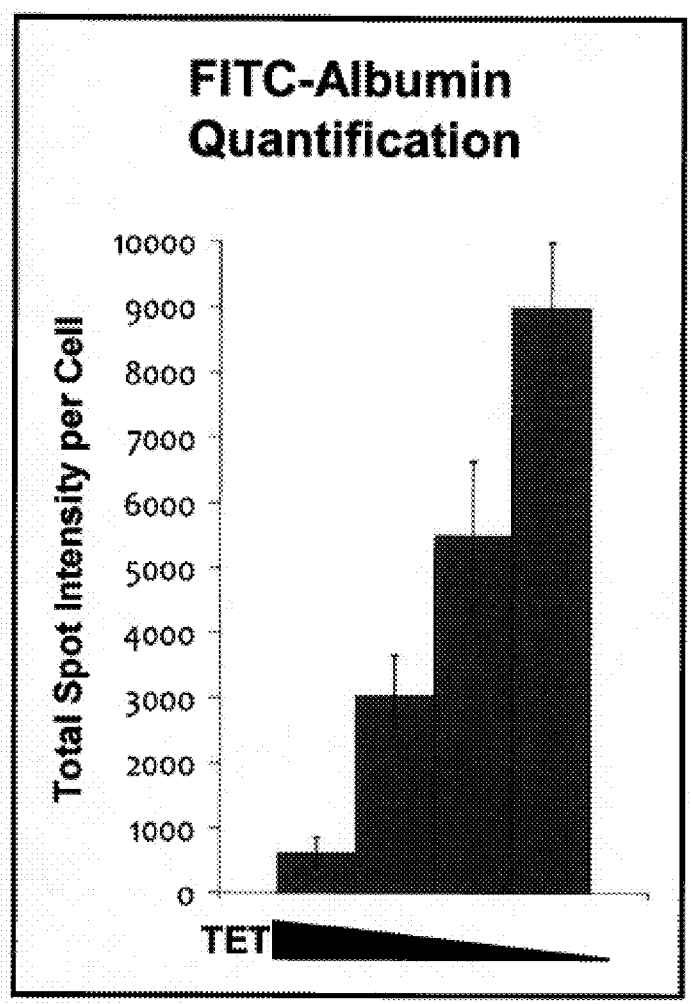
Figures 7A, 7B, 7C:
FIGS. 7A-7C show albumin internalization co-localizes with dextran-positive macropinosomes.
Figure 8A:
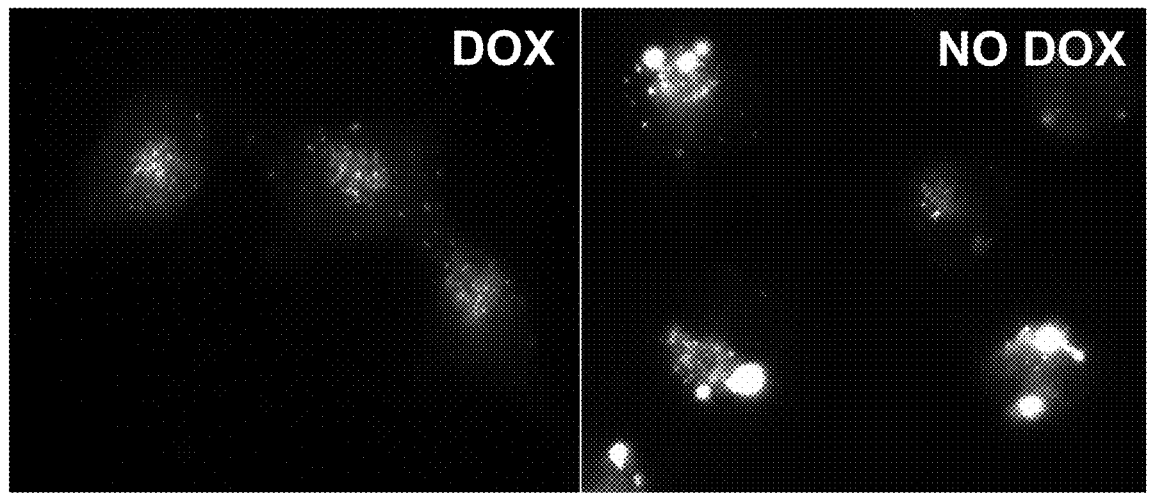
FIGS. 8A-8B show that acidic cellular compartments are increased in oncogenic Ras$^{V12}$-expressing HeLa cells.
Figure 8B:
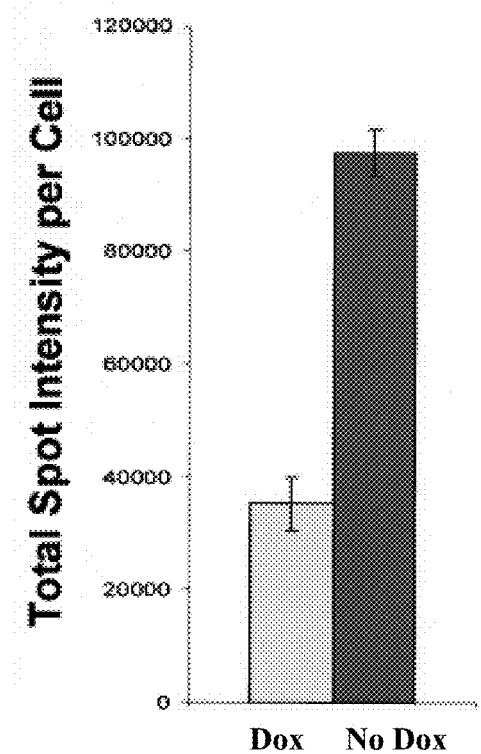
Figure 9A:
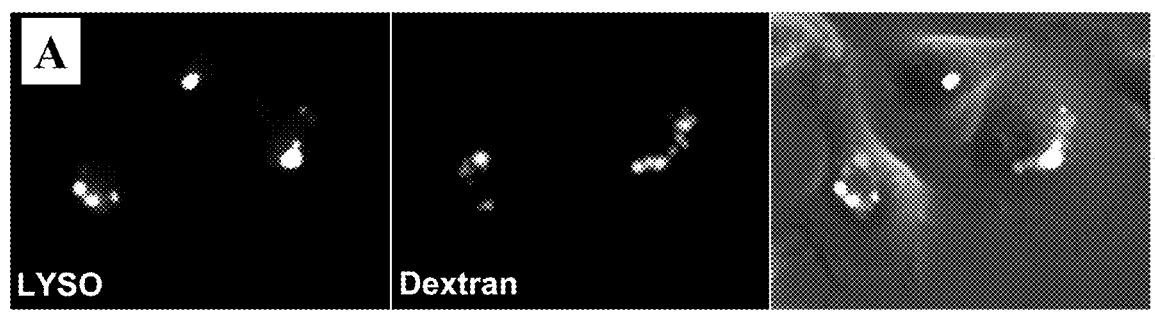
FIGS. 9A-9B demonstrate that macropinosome contents are destined for an acidic cellular compartment. The fate of the macropinosomes was followed via pulse chase experiments and their fusion with lysosomes was monitored by co-staining with lysosomal markers (i.e., Lysotracker.
Figure 9B:
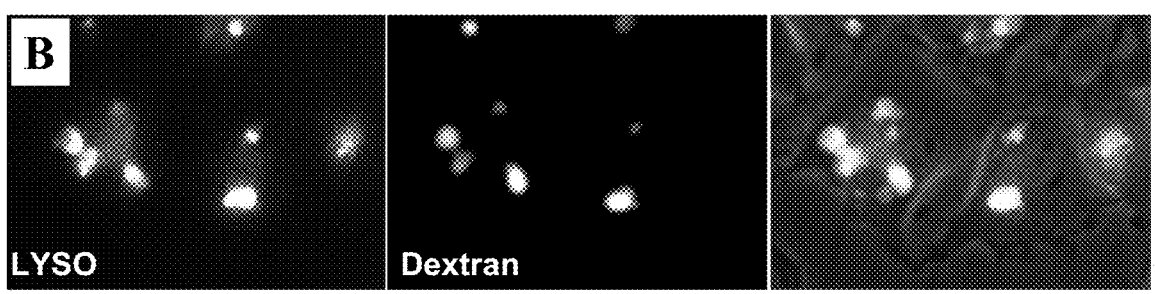

When added to the growth medium, fluorescently-labeled bovine serum albumin (FITC-BSA) was incorporated into vesicular compartments in oncogenic Ras$^{V12}$-expressing HeLa cells (FIG. 6A), MIA-Paca-2, and T24 cells. This internalization process was inhibited by EIPA, suggesting that cancer cells harboring Ras mutations can internalize extracellular protein via macropinocytosis. Quantification of FITC-BSA uptake was performed utilizing an amended form of the high-throughput protocol described herein (FIG. 6B). Using colocalization experiments, it was observed that FITC-BSA is internalized with a macropinocytosis marker, dextran (FIG. 7A-7C). To be utilized as a nutrient source, the protein contents of Ras-stimulated macropinosomes must be delivered to a degradative compartment, such as the lysosome. The fate of the macropinosomes was followed via pulse chase experiments and their fusion with lysosomes was monitored by co-staining with lysosomal markers (i.e. Lysotracker). Cells were pulsed with TMR-dextran and incubated with TMR-dextran-free media for varying intervals. At the end of the incubation period, cells were stained with a lysosomal marker and visualized by fluorescent microscopy. FIG. 9 shows that macropinsome contents are destined for an acidic lysosomal compartment.

Figure 10A:
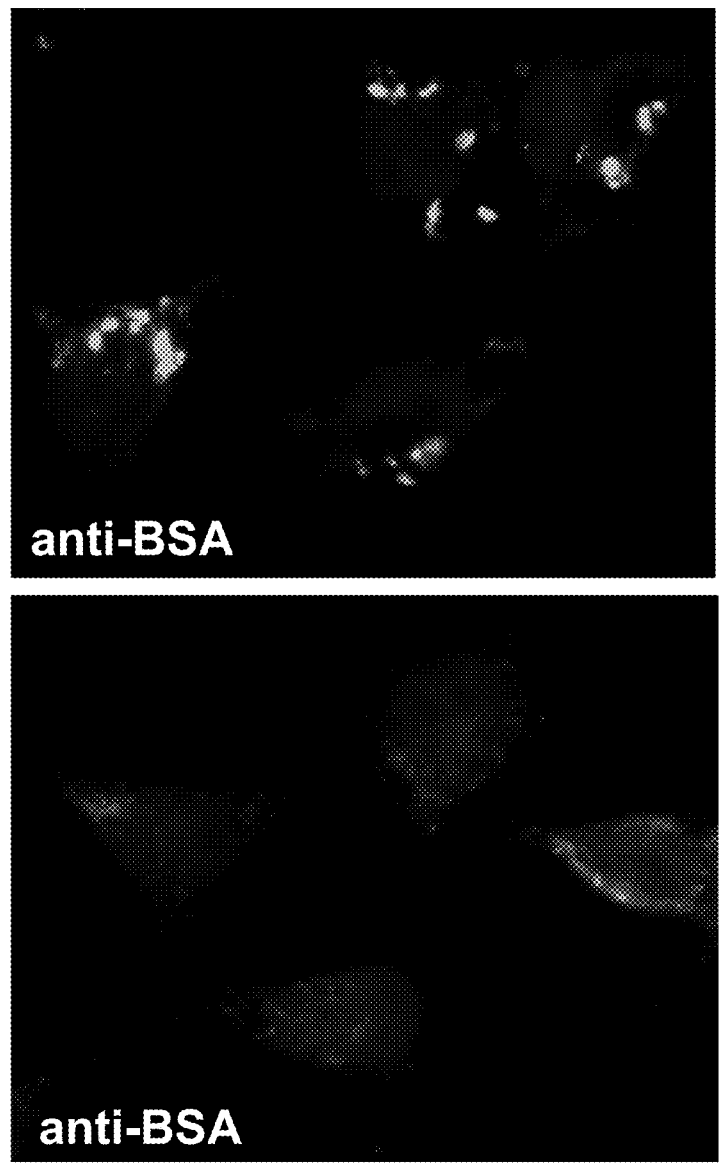
FIGS. 10A-10B depict albumin catabolism in oncogenic Ras$^{V12}$-expressing HeLa cells. Albumin degradation was measured via a pulse-chase experiment consisting of incubating pancreatic cancer cells with BSA and subsequently chasing with BSA-free media. The presence of internalized BSA was measured by immunostaining the cells with an anti-BSA antibody and a fluorescent secondary antibody (FIG. 10A). The top panel of FIG. 10A shows anti-BSA staining in the absence of chasing in BSA-free media (T=0) and the bottom of panel
Figure 10B:
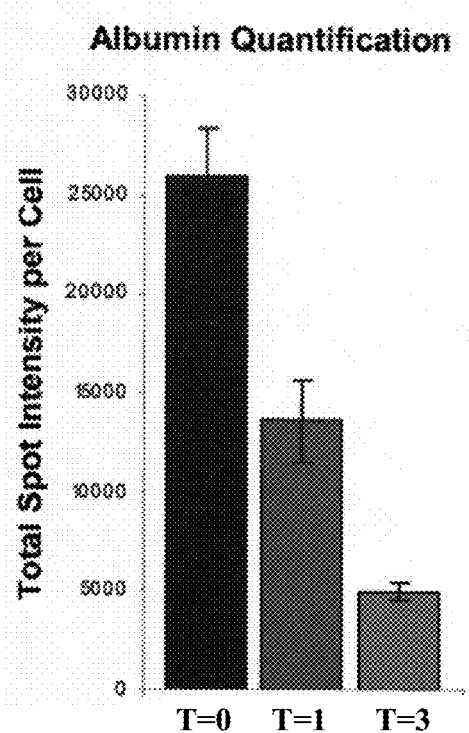

Albumin degradation was measured via a pulse-chase experiment consisting of incubating oncogenic Ras$^{V12}$-expressing HeLa cells with BSA and subsequently chasing with BSA-free media. The presence of internalized BSA was measured by immunostaining the cells with an anti-BSA antibody and a fluorescent secondary antibody (FIG. 10A). Subsequently, the intensity of the fluorescent signal that was incorporated into vesicular spots was quantified using automated spot detection (FIG. 10B).

Figures 11A, 11B:
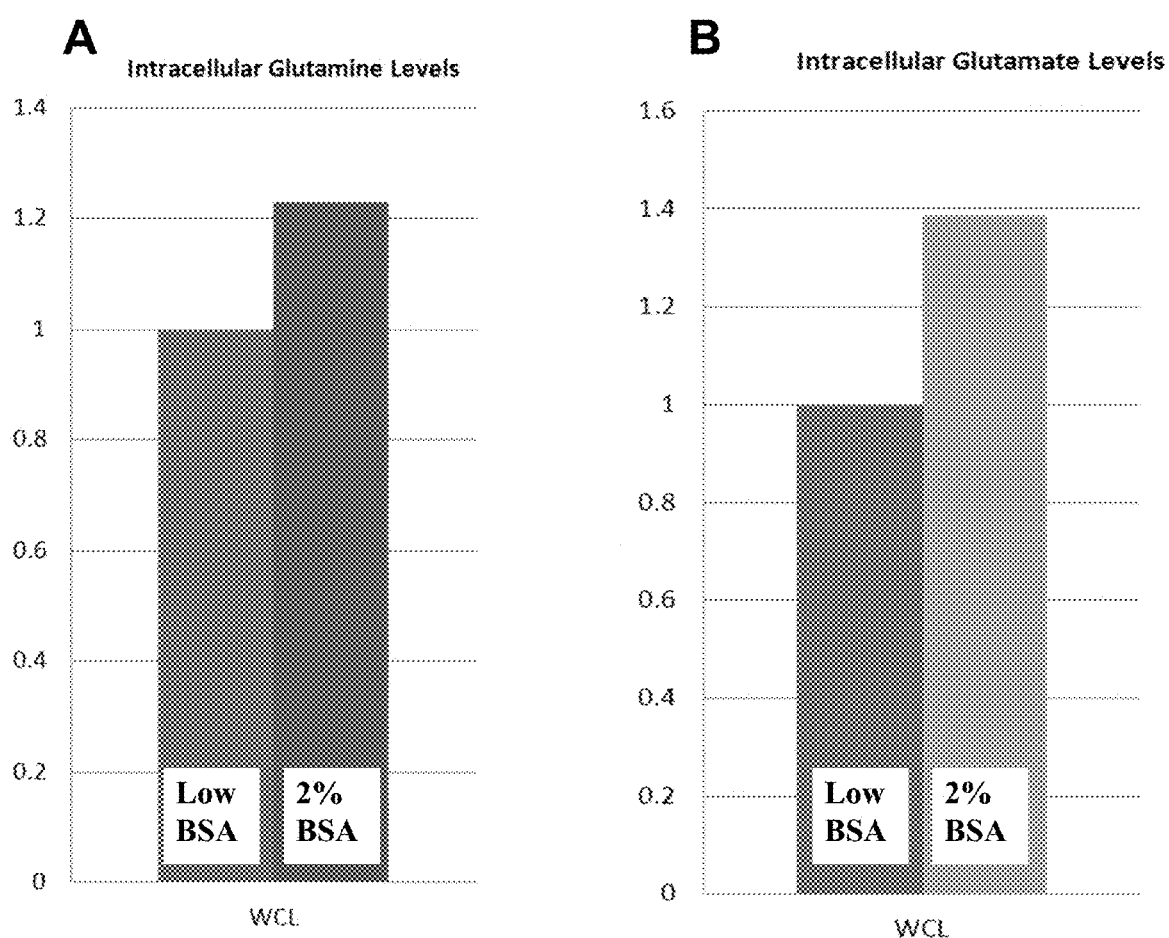
FIGS. 11A-11B demonstrate that glutamine (FIG. 11A) and glutamate (FIG. 11B) production in NIH 3T3 cells transformed by oncogenic K-Ras is increased in the presence of physiological levels of albumin (i.e., 2%).

To demonstrate that glutamine and glutamate production results from the degradation of albumin, K-Ras transformed NIH 3T3 cells were incubated with either low (0.4%) or physiological (2%) concentrations of albumin for 24 hours. Cells were harvested and the intracellular glutamine (FIG. 11B) and glutamate (FIG. 11B) concentration was determined using the EnzyChrom Glutamine Assay Kit (BioAssay Systems).

Example 5—Survival and Growth of Oncogenic Ras Expressing Cells in Low Glutamine Conditions Glutamine, the most abundant amino acid in mammals, is required for tumor cell proliferation and is critical to tumor cell bioenergetics and macromolecular biosynthesis (DeBerardinis et al., "The Biology of Cancer: Metabolic Reprogramming Fuels Cell Growth and Proliferation," *Cell Metab.* 7(1):11-20 (2008), which is hereby incorporated by reference in its entirety). Under physiological conditions, glutamine is supplied by interstitial fluids and blood plasma and is internalized by cells via various glutamine transport systems (McGivan et al., "The Transport of Glutamine into Mammalian Cells," *Front Biosci.* 12:874-82 (2007), which is hereby incorporated by reference in its entirety). In tumor cells, however, the rate of glutamine consumption is markedly increased leading to the depletion of free glutamine (Medina "Glutamine and cancer," *J. Nutr.* 131(9 Suppl): 2539S-42S (2001), which is hereby incorporated by reference in its entirety). Therefore, glutamine availability to the tumor may become limiting, invoking the need for alternative glutamine sources. Physiological fluids are composed of up to 70% protein, most of which is serum albumin, a potentially rich source of amino acids for tumor cells (Stehle et al., "Plasma Protein (Albumin) Catabolism by the Tumor Itself—Implications for Tumor Metabolism and the Genesis of Cachexia," *Crit. Rev. Oncol. Hematol.* 26(2)77-100 (1997), which is hereby incorporated by reference in its entirety). The data herein indicate that the internalization of extracellular serum albumin via macropinocytosis, an endocytic mechanism of fluid-phase uptake, can serve to augment the glutamine supply (FIGS. 11A-11B) and that this mechanism contributes to pancreatic cancer cell growth and survival.

Figure 12A:
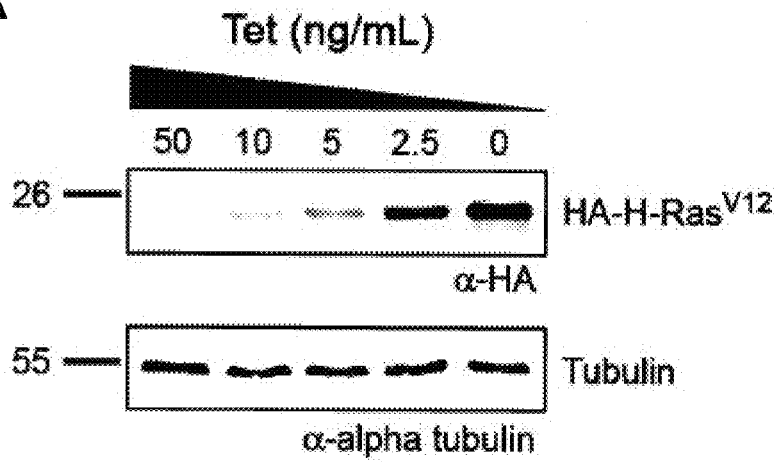
FIGS. 12A-12B show that oncogenic Ras-expressing HeLa cells have a survival advantage when deprived of glutamine in the presence of conventional albumin-containing medium.
Figure 12B:
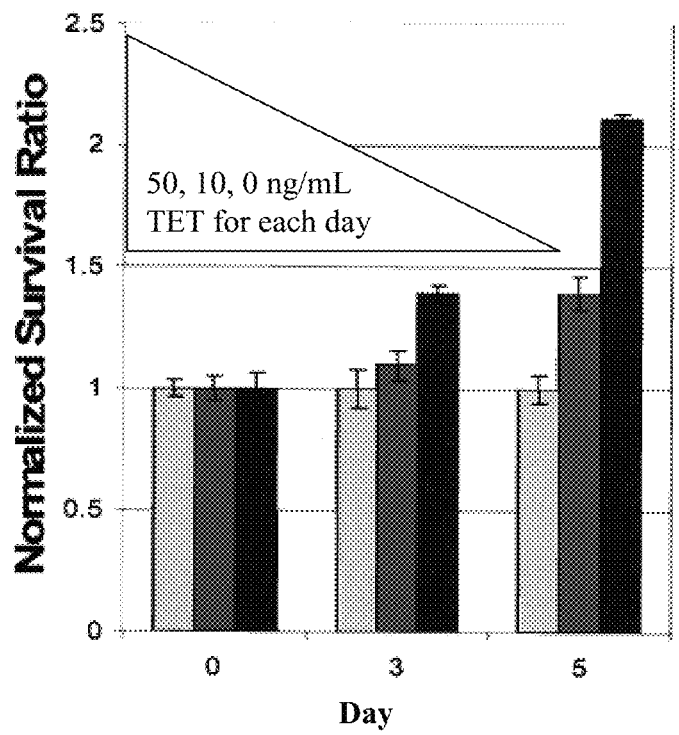
Figure 13:
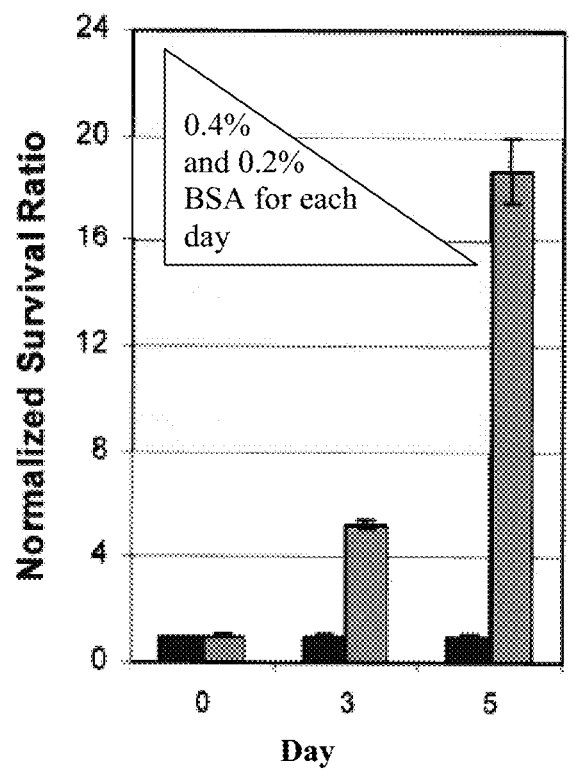
FIG. 13 demonstrates that increasing the protein content of the media (0.4% or 2% albumin) enhances viability of oncogenic Ras$^{V12}$-expressing HeLa cells.
Figure 14A:
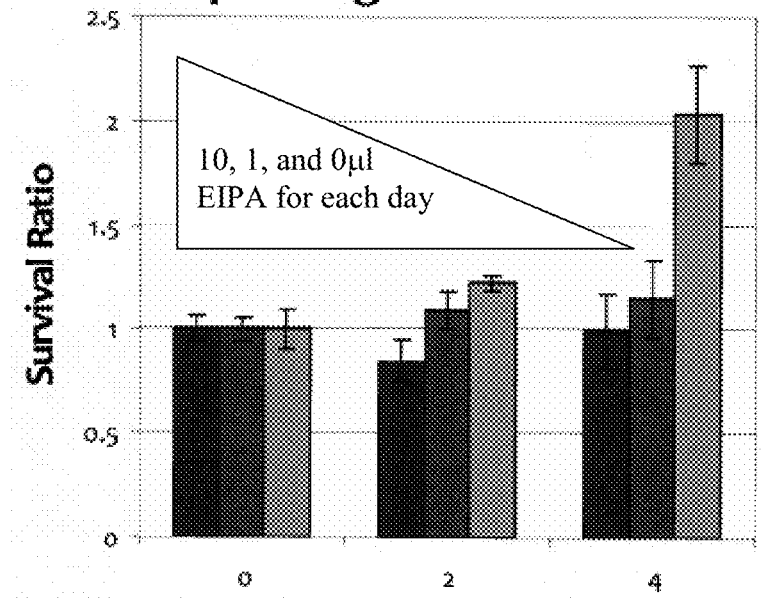
FIGS. 14A-14B show that the survival advantage of oncogenic Ras-expressing HeLa cells in glutamine-free media containing low BSA (FIG. 14A) or 2% BSA (FIG. 14B) is suppressed by EIPA, a macropinocytosis inhibitor.
Figure 14B:
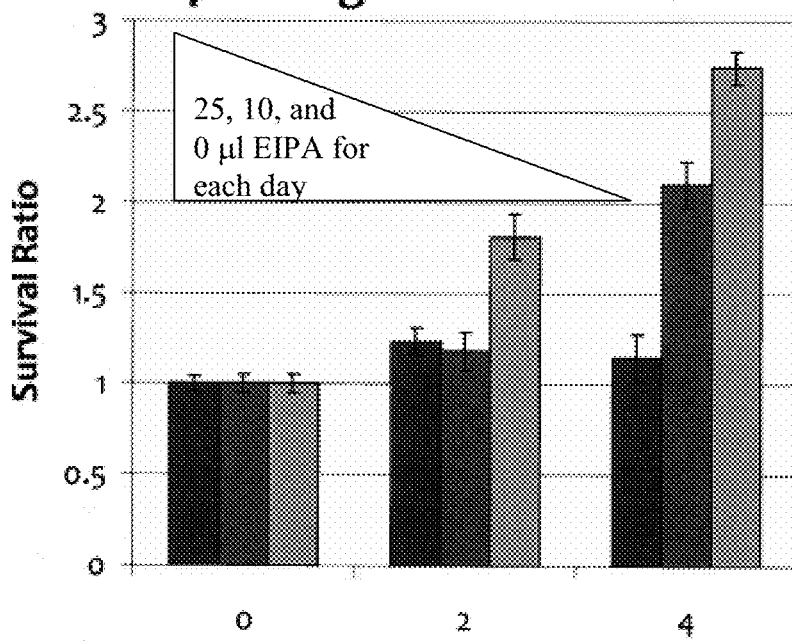

If albumin internalization via Ras-stimulated macropinocytosis serves to augment the glutamine supply, then this process should confer a survival and growth advantage under conditions where free glutamine is limiting. To test this prediction, the survival of oncogenic $Ras^{V12}$-expressing HeLa cells was tested. Under glutamine starvation (0 mM) conditions and in the presence of low albumin concentrations (0.2%), the $Ras^{V12}$-expressing cells exhibit a survival advantage (FIG. 12B). It was hypothesized that this was due to albumin-derived amino acids that were augmenting the intracellular glutamine supply. It was determined that $Ras^{V12}$-survival was enhanced at higher concentrations of extracellular albumin (up to 2%; FIG. 13) and that this survival enhancement was suppressed by EIPA, a macropinocytosis inhibitor (FIGS. 14A-14B).

Figure 15:
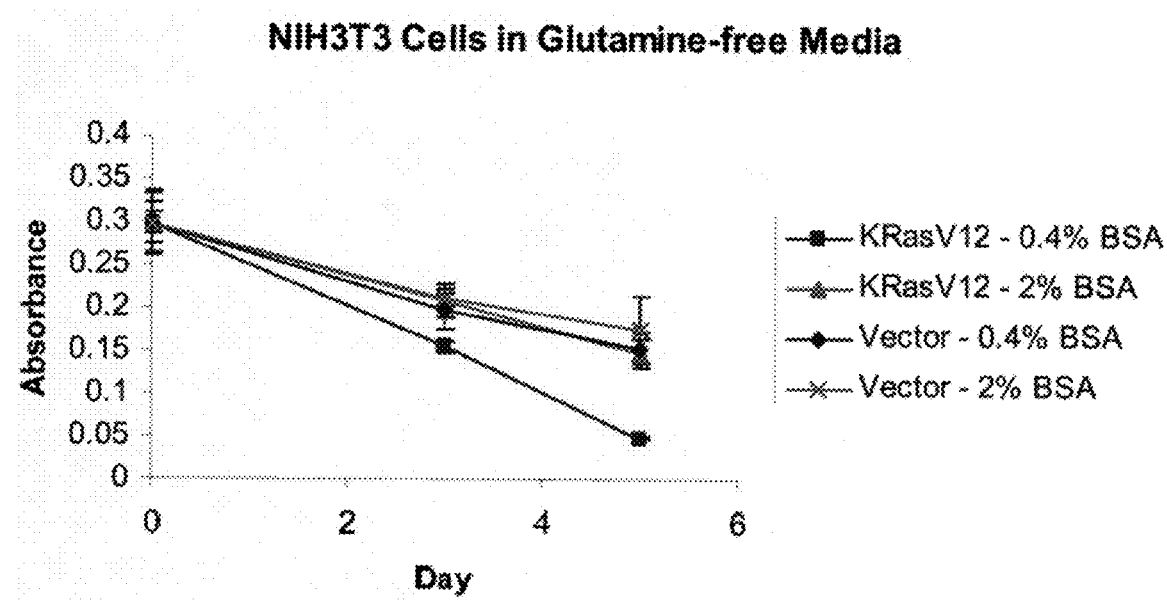
FIG. 15 shows that extracellular BSA partially rescues K-Ras transformation-associated glutamine addiction in NIH 3T3 cells. The graph depicts cell viability over time.
Figures 17A, 17B:
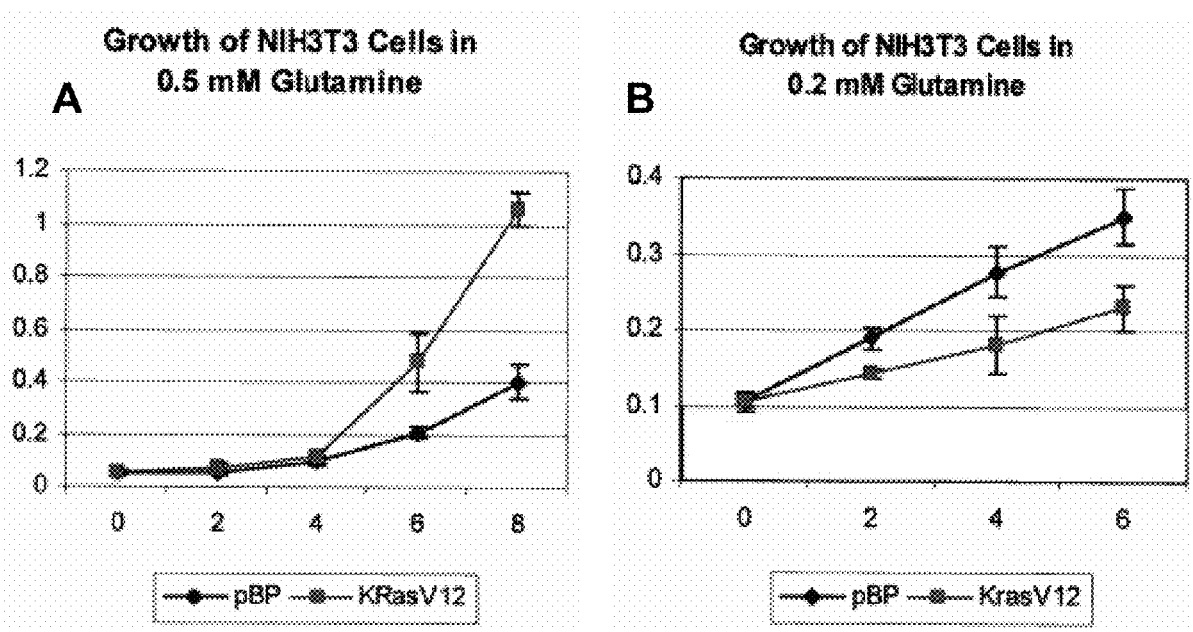
FIGS. 17A-17B are graphs charting cell growth of K-Ras$^{V12}$-transformed NIH 3T3 cells and vector only controls in physiological (FIG. 17A) and sub-physiological levels (FIG. 17B) of glutamine.

These findings were extended by analyzing glutamine-deprivation and survival in K-Ras-transformed NIH 3T3 cells. $K-Ras^{V12}$-expressing NIH3T3 cells are exquisitely sensitive to glutamine deprivation and the glutamine addiction displayed by these cells is selectively and partially rescued by increasing the concentration of extracellular albumin (FIG. 15). These findings were corroborated by the analyses in cancer cell lines harboring Ras-mutations, which yielded similar results (FIG. 16).

Figures 18A, 18B:
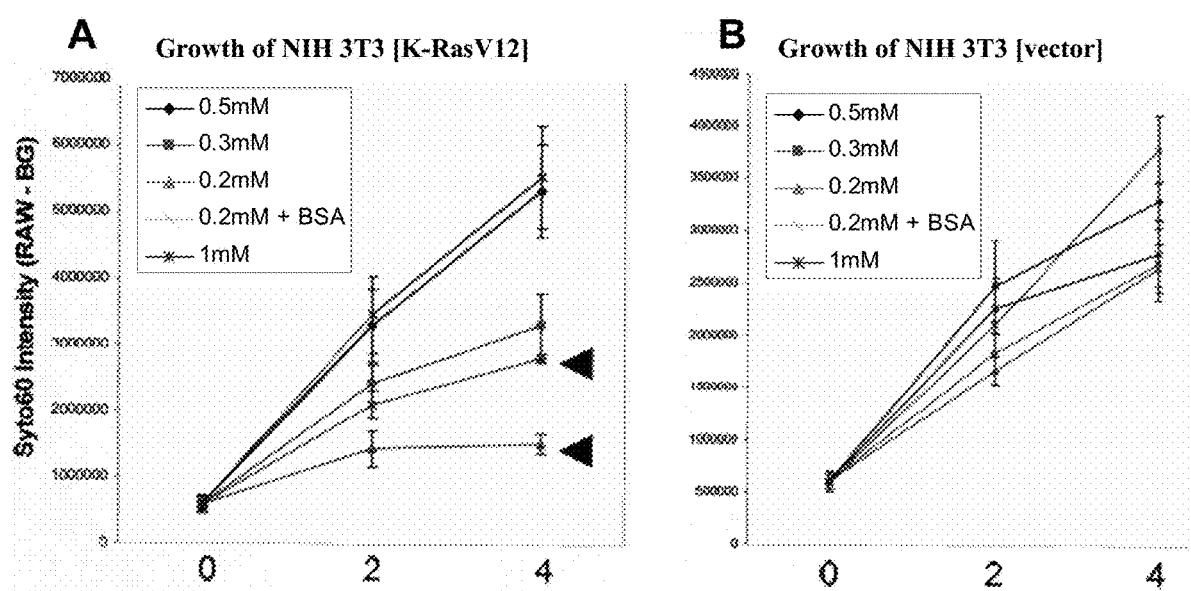
FIGS. 18A-18B are graphs showing the effect of increasing protein content of the growth media on cell proliferation in K-Ras$^{V12}$-transformed NIH 3T3 cells (FIG. 18A) and control cells (FIG. 18B) in sub-physiological glutamine conditions.
Figures 19A, 19B:
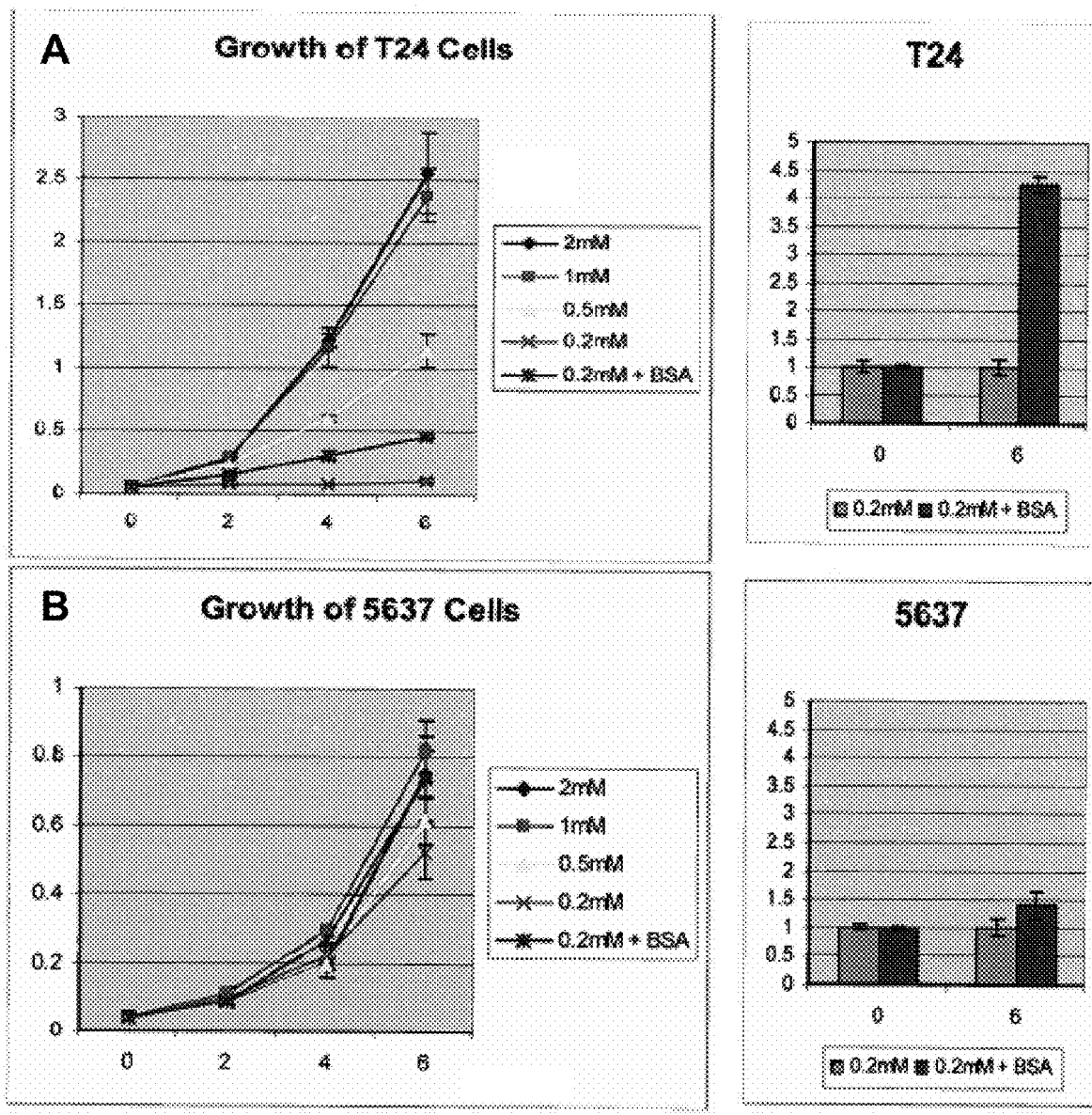
FIGS. 19A-19B demonstrate that extracellular BSA partially rescues glutamine addiction selectively in T24 cells (FIG. 19A) harboring an oncogenic Ras mutation, and not 5637 cells (FIG. 19B) which have a non-mutant Ras gene.

Next, whether the proliferative defect of cancer cells in low glutamine (0.2 mM) can be rescued by the supplementation of the growth medium with physiological concentrations of serum albumin (2-4%) was examined. This was determined to be the case using $K-Ras^{V12}$-expressing NIH3T3 cells (FIG. 18). Additionally this observation was noted in T24 cells, which harbor oncogenic H-Ras, but not in 5637 cells, which only express wild-type H-Ras (FIGS. 19A-19B).

Figure 20A:
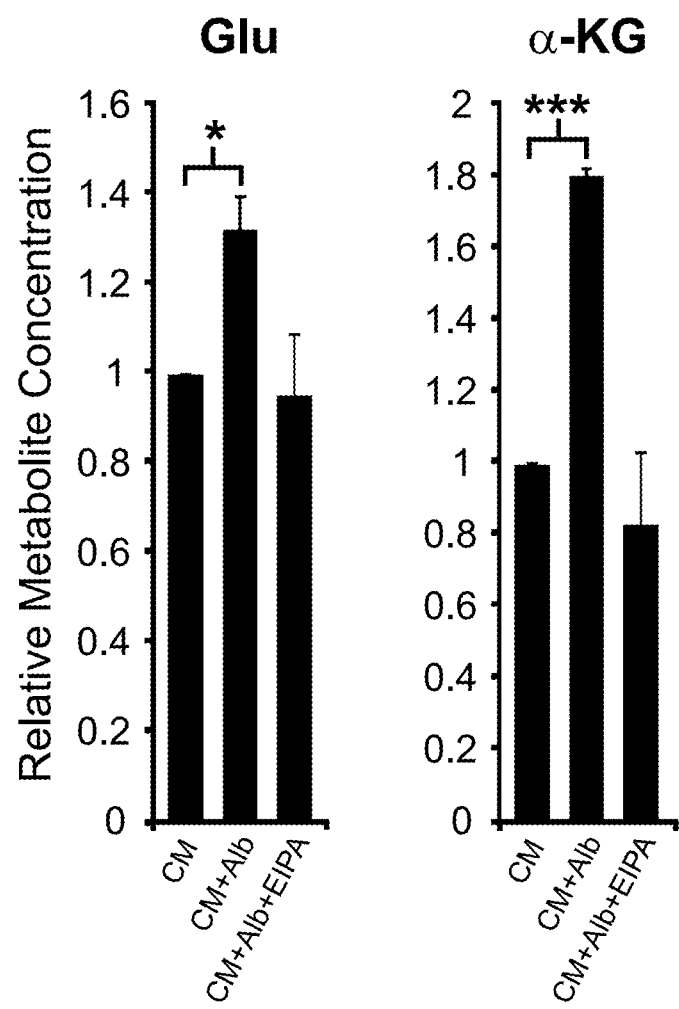

Example 6—Albumin Supplementation and Cell Growth are Connected to Glutamine Metabolism Glutamine is a major nutrient for many proliferating cells and is rapidly metabolized to glutamate, then α-ketoglutarate to enter central carbon metabolism. To test whether the favorable effects of albumin supplementation on cell growth were related to glutamine metabolism, the intracellular concentrations of glutamate and α-ketoglutarate in cells grown either in the absence or presence of albumin was measured. NIH 3T3 [$K-Ras^{G12V}$] cells were cultured for 24 hours in complete media (CM) supplemented to physiological concentrations of albumin (2 g/100 mL, 2%). As a control, NIH 3T3 [$K-Ras^{G12V}$] cells were also cultured in CM alone, which contains minimal levels of albumin (~0.2%). Cells were lysed and metabolite levels were determined from deproteinized cell lysates. The addition of albumin to the media led to significant increases in intracellular concentrations of both glutamate and α-ketoglutarate (FIG. 20A). These albumin-dependent increases in both glutamate and α-ketoglutarate were blocked by EIPA treatment (FIG. 20A), suggesting that macropinocytic uptake of albumin can promote accumulation of glutamine catabolic intermediates in oncogenic Ras-transformed cells. Consistent with this idea, the anti-proliferative response to EIPA observed in the presence of physiological albumin was rescued by increased levels of glutamine and by exogenous α-ketoglutarate (FIG. 20B). Together, these data suggest that the macropinocytic uptake of albumin facilitates proliferation under low glutamine conditions due to the intracellular production of glutamine and potentially other amino acids.

In order for the macropinocytosis of albumin to constitute a mechanism of amino acid supply, the internalized albumin would have to be destined for proteolytic degradation. To detect intracellular degradation of albumin, a highly self-quenched BODIPY dye conjugated form of BSA (DQ-BSA) that only emits a bright fluorescent signal upon proteolytic digestion was utilized. Dual labeling of NIH 3T3 [$K-Ras^{G12V}$] cells with DQ-BSA and TMR-dextran was used to determine the macropinocytic origin of the degradative compartment. In cells that were immediately fixed following a 30 minute incubation with DQ-BSA and TMR-dextran (T=0), there was no appreciable DQ-BSA fluorescence detected in macropinosomes (FIG. 20C). However, in cells that were incubated for 30 minutes and subsequently chased for 1 hour in media free of both DQ-BSA and TMR-dextran, a significant level of DQ-BSA fluorescence was detected in TMR-positive macropinosomes (FIG. 20C). DQ-BSA fluorescence was also detected within macropinosomes after a 1 hour chase in MIA PaCa-2 and T24 cells, indicating that these trafficking events were also occurring in cancer cells harboring endogenous oncogenic Ras mutations. These data demonstrate that oncogenic Ras-expressing cells can harness macropinocytosis for the internalization and degradation of extracellular albumin, and raise the possibility that albumin-derived amino acids may accumulate intracellularly.

Example 7—A High Throughput-Compatible Macropinocytosis Assay

To analyze and quantify Ras-stimulated macropinocytosis, a high content screening (HCS)-compatible platform designed for rapid spot analysis was desired. One such platform is the Arrayscan HCS Reader (Cellomics) in conjunction with the Spot Detector BioApplication (Cellomics), which is designed to provide fluorescent- and image-based generic spot analysis for multiple biological applications. As a model cell-based system, a HeLa Tet-Off (HTO) cell line (Clontech) stably transfected with a tetracycline-repressible transgene encoding an oncogenic form of hemagglutinin (HA)-tagged H-Ras (H-$Ras^{V12}$) was used. In brief, 2000 cells per well were plated in 384-well plate format in a total volume of 50 μL. To induce expression of H-$Ras^{V12}$, cells were plated in media lacking tetracycline, while control cells were plated in 50 ng/mL tetracycline. Twenty-four hours after plating, cells were washed one time with PBS and incubated for 24 hours in serum-free media (either containing 50 ng/mL tetracycline or tertacycline-free). The macropinocytosis assay consisted of the addition of a 70 kDa tetramethylrhodamine-labelled dextran (TMR-dextran, Invitrogen) to the media. After a 30 minute incubation period, cells were washed twice with cold PBS, fixed and DAPI-stained.

Figures 21A, 21B:
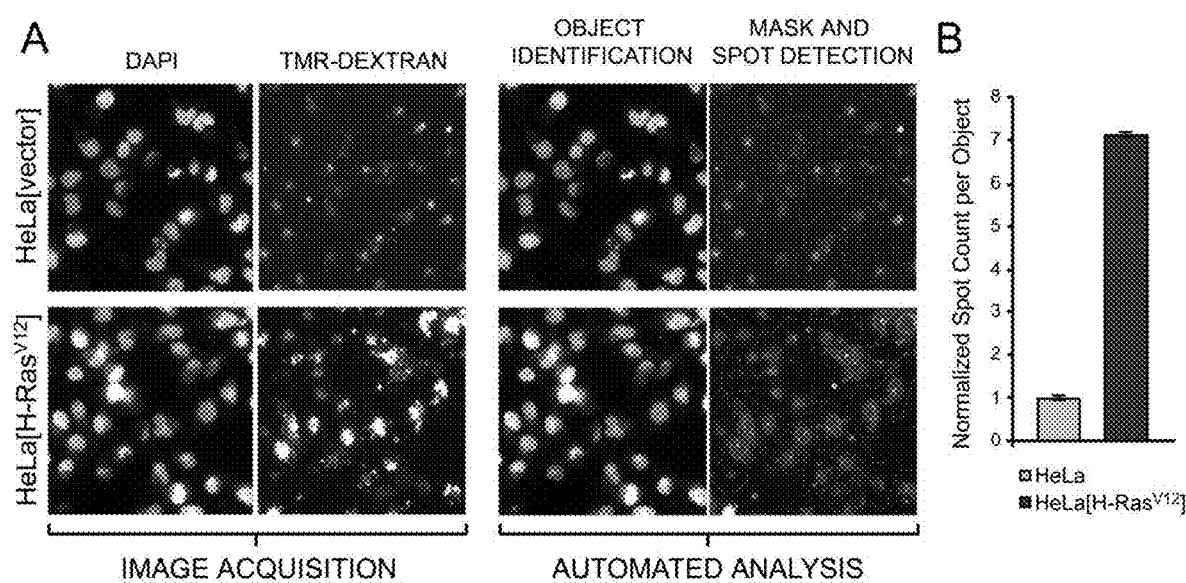
FIGS. 21A-21B show the high-throughput quantification of macropinocytosis in HeLa cells expressing Oncogenic Ras$^{V12}$.

Macropinosomes were analyzed on a cell-to-cell basis using multichannel analysis on the Arrayscan HCS Reader (FIG. 21A). Primary objects (cells) were located by the DAPI stained nuclei on Channel 1. A circular spot identification target region (or mask) was then applied for each object on Channel 2, and spots were detected based on their fluorescent intensity, size, and shape. As expected, spot identification was significantly higher in cells expressing oncogenic H-Ras (FIG. 21A, compare the right-most images with HeLa [vector] only shown in the top image and HeLa[H-Ras$^{V12}$] shown in the bottom image, spot identification is shown in red). To quantify this, the output feature selected for Channel 2 was Spot Count Per Object, which is effectively a measure of total number amount of fluorescent extracellular fluid internalized per cell in a given incubation time. H-Ras$^{V12}$-expressing cells have a 8- to 9-fold increase in the levels of fluid-phase uptake compared to cells assayed in tetracycline (FIG. 21B).

One of the advantages of using the Tet-Off repression system is that levels of the transgene of interest can be finely controlled via the concentration of tetracycline supplemented to the medium. With decreasing levels of tetracycline, levels of H-Ras$^{V12}$ are increased (FIG. 12A) and resulting in a concomitant increase in fluid-phase uptake (FIG. 1B). Varying tetracycline concentrations did not affect macropinocytosis in the parental HTO cell line, demonstrating that the stimulation of macropinocytosis is directly correlated to levels of H-Ras$^{V12}$ expression.

An advantage to using the Spot Detector BioApplication is that in addition to well-level features, the software also provides field-level results. Field-level data can be useful in high-throughput analyses to determine the intra-well variation. Within a given concentration of tetracycline, the spot total intensity per object did not vary greatly, however, cells grown in tetracycline-free media had the greatest difference compared to control cells.

To determine the feasibility of using this high throughput assay to identify novel chemical inhibitors of Ras-stimulated macropinocytosis, the effects of known macropinocytosis inhibitors were evaluated. The activation of phosphoinositide 3-kinases (PI3Ks) is required for the stimulation of macropinocytosis. PI3Ks are potently inhibited by 2-(4-morpholinyl)-8-phenyl-4H-1-benzopyran-4 (LY294002), which exerts its effects by selectively targeting the ATP-binding site of the kinase. The effects of LY294002 on Ras-stimulated macropinocytosis were assessed using this HT assay.

Figure 22A:
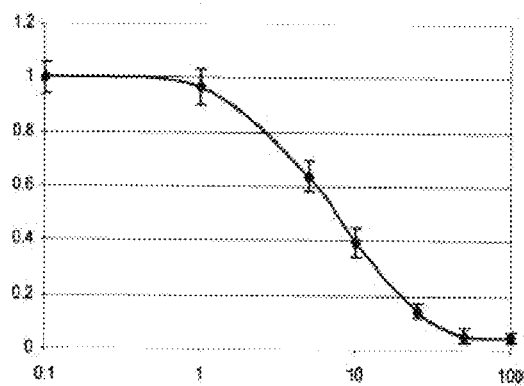
FIGS. 22A-22B show the dose-response analyses for the macropinocytosis inhibitors LY294002 (FIG. 22A) and EIPA (FIG. 22B) using the high-throughput compatible macropinocytosis assay in oncogenic Ras$^{V12}$-expressing HeLa cells.

HeLa cells expressing HA-H-Ras$^{V12}$ were plated in 384-well format at 2500 cells per well. After 24 hours, cells were washed with PBS and growth media was replaced with serum free media and incubated for 24 hours. For the inhibition assay, cells were pre-incubated with various concentrations of LY294002 in serum-free media for 30 minutes. This was followed by the addition of TMR-dextran for 30 minutes and plates were subsequently processed as described earlier. High content analysis revealed a dose-response relationship with maximal inhibition of macropinocytosis occurring at 100 µM LY294002 (FIG. 22A).

Macropinocytosis is also potently inhibited by Na$^+$/H$^+$ exchanger inhibitors such as amiloride and its analogs. Amiloride likely exerts its effects on macropinoctyosis by lowering the submembranous pH and interfering with the activation of GTPases that promote actin remodeling. EIPA, an amiloride analog, selectively inhibits the Na$^+$/H$^+$ exchanger, is soluble in cell culture media, and exerts its effects at much lower concentrations (50-100 µM) compared to amiloride (1-5 mM). Therefore, EIPA treatment was used to further validate the high throughput assay.

Figure 22B:
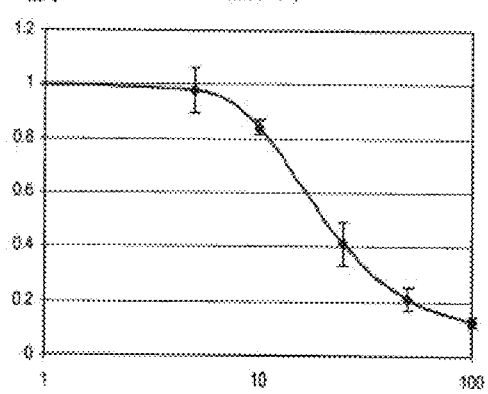

The inhibition assay using EIPA was similar to that described for LY294002. Treatment with EIPA resulted in a dose-response relationship with maximal inhibition of macropinocytosis occurring at 100 µM (FIG. 22B)

To explore the flexibility of the high-throughput compatible macropinocytosis assay, the HeLa-based Spot Detector BioApplication parameters were amended to quantify macropinocytosis in K-Ras$^{V12}$-expressing NIH3T3 cells. To do this, object identification parameters were altered to accommodate larger nuclei and the spot identification target region was adjusted accordingly.

Untransformed NIH3T3 cells display low levels of macropinocytosis, compared to K-Ras$^{V12}$-transformed cells. Using this amended protocol, it was possible to quantify fluid-phase uptake in these cells and determine that K-Ras$^{V12}$-expressing cells have a 3-4 fold increase in macropinocytosis (FIGS. 2A-2B). To examine the effects of macropinocytosis inhibitors, K-Ras$^{V12}$-transformed NIH3T3 cells were treated with increasing concentrations of LY294002 or EIPA. Quantification of macropinocytosis via the high-throughput assay revealed a dose-response relationship for both inhibitors. Altogether, these data indicate that the high-throughput-compatible macropinocytosis assay of the present invention can be amended to accommodate other cell types, and that known macropinocytosis inhibitors have a measurable effect on both H-Ras- and K-Ras-stimulated macropinocytosis.

Although the invention has been described in detail for the purpose of illustration, it is understood that such detail is solely for that purpose, and variations can be made therein by those skilled in the art without departing from the spirit and scope of the invention which is defined in the following claims.

---

What is claimed:

1. A method comprising:
   selecting a subject having cancer;
   administering to the selected subject an agent selected from the group consisting of dextran, albumin, poly(beta-amino ester) nanoparticles, polyethylenimine-alt-poly(ethylene glycol) copolymer nanoparticles, and lipid nanoparticles;
   detecting the presence of the agent in cells of the subject; and
   quantifying the presence of the agent in cancerous cells and non-cancerous cells of the subject.

2. The method according to claim 1, wherein the selected subject has an oncogene mediated cancer.

3. The method according to claim 2, wherein the oncogene mediated cancer is selected from the group consisting of ras-mediated cancer, src-mediated cancer, and EGFR-mediated cancer.

4. A method according to claim 1, wherein the selected subject has a cancer selected from the group consisting of pancreatic cancer, lung cancer, colorectal cancer, thyroid cancer, liver cancer, and leukemia.

5. The method according to claim 1, wherein the agent is labeled with a fluorescent label, a bioluminescent label, or a radioisotope.

6. The method according to claim 1, further comprising: administering a chemotherapeutic agent to the subject based on said quantifying.

7. The method according to claim 1, further comprising: administering a macropinocytosis inhibitor to the subject based on said quantifying, wherein said macropinocytosis inhibitor is selected from the group consisting of wortmannin, LY294002, amiloride, and an analogue of amiloride.

* * * * *